United States Patent [19]
Nabel et al.

[11] Patent Number: 5,733,543
[45] Date of Patent: Mar. 31, 1998

[54] INTRODUCTION OF HIV-PROTECTIVE GENES INTO CELLS BY PARTICLE-MEDIATED GENE TRANSFER

[76] Inventors: Gary J. Nabel, 3390 Andover Rd.; Clive Woffendin, 3509 Burbank Dr., both of Ann Arbor, Mich. 48105; Nin-Sun Yang, 7802 Oxtrail Way, Verona, Wis. 53593; Michael J. Sheehy, 629 Piper Dr., Madison, Wis. 53711

[21] Appl. No.: 235,277

[22] Filed: Apr. 29, 1994

[51] Int. Cl.$^6$ .......................... A01N 63/00; A61K 48/00
[52] U.S. Cl. .......................... 424/93.21; 514/44; 935/59
[58] Field of Search .................. 514/44; 435/240.1, 435/320.1, 172.3, 91.1; 424/93.1, 93.2, 93.21; 536/24.5; 935/59

[56] References Cited

U.S. PATENT DOCUMENTS

| | | | |
|---|---|---|---|
| 4,945,050 | 7/1990 | Sanford et al. | 435/172.1 |
| 5,015,580 | 5/1991 | Christou et al. | 435/172.3 |
| 5,120,657 | 6/1992 | McCabe et al. | 435/287 |
| 5,306,631 | 4/1994 | Harrison et al. | 435/172.3 |
| 5,324,643 | 6/1994 | Greatbatch et al. | 435/91.32 |

OTHER PUBLICATIONS

Bahner, I. et al. "Comparison of Trans–Dominant Inhibitory . . . " J. Virology 67(6): 3199–3207 (Jun. 1993).

Burkholder, JK et al. "Rapid Transgene Expression in Lymphocyte . . . " J. of Immunological Methods 165: 149–156 (1993).

Dropulic, B. et al. "Gene Therapy for Human Immunodeficiency Virus Infection . . . " Human Gene Therapy 5: 927–939 (Aug. 1994).

Gilboa, E. et al. "Gene Therapy for Infectious Diseases: The AIDS Model" Trends in Genetics 10(4): 139–144 (Apr. 1994).

Heiser, WC. "Gene Transfer Into Mammalian Cells by Particle Bombardment", Analytical Biochemistry 217: 185–196 (1994).

Malim, MH et al. "Stable Expression of Transdominant Rev Protein . . . " J. Exp. Med. 176: 1197–1201 (1992).

Marshall, E. "Gene Therapy's Growing Pains", Science 269: 1050–1055 (Aug. 1995).

Journal of Immunological Methods, vol. 165, No. 2, Oct. 15, 1993, J.K. Burkholder, et al., "Rapid Transgene Expression in Lymphocyte and Macrophage Primary Cultures After Particle Bombardment–Mediated Gene Transfer", pp. 1–20.

Proc. Natl. Acad. Sci. USA, vol. 87, No. 24, Dec. 1990, N.S. Yang, et al., "In Vivo and In Vitro Gene Transfer to Mammalian Somatic Cells by Particle Bombardment", pp. 9568–9572.

Bio/Technology, vol. 11, pp. 497–502, Apr. 1993, S. Jiao, et al., "Particle Bombardment–Mediated Gene Transfer and Expression in Rat Brain Tissues".

In Vitro Cell. Dev. Biol., vol. 29A, pp. 165–170, Feb. 1993, T.A. Thompson, et al., "Transient Promoter Activity in Primary Rat Mammary Epithelial Cells Evaluated Using a Particle Bombardment Gene Transfer".

Proc. Natl. Acad. Sci. USA, vol. 90, pp. 4455–4459, May 199S, L. Cheng et al., "In Vivo Promoter Activity and Transgene Expression in Mammalian Somatic Tissues Evaluated by Using Particle Bombardment".

Critical Reviews in Biotechnology, vol. 12, No. 4, pp. 335–356, 1992, Ning–Sun Yang, Ph.D., "Gene Transfer Into Mammalian Somatic Cells In Vivo".

Medical Sciences, pp. 1–28, C. Woffendin, et al., "Non–Viral Delivery of an HIV Protective Gene Into Primary Human T Cells".

(List continued on next page.)

*Primary Examiner*—Bruce R. Campell
*Attorney, Agent, or Firm*—Oblon, Spivak, McClelland, Maier & Neustadt, P.C.

[57] ABSTRACT

Foreign genes may be stably introduced into T cells, monocytes, macrophages, dendrites, and hematopoietic stem cells by particle-mediated gene transfer. Introduction of an HIV protective gene into the cells of a patient infected with HIV by particle-mediated gene transfer is effective for the treatment of HIV infection.

20 Claims, 23 Drawing Sheets

OTHER PUBLICATIONS

J. Exp. Med., vol. 176, pp. 1197–1201, Oct. 1992, M.H.Malim, et al., "Stable Expression of Transdominant Rev Protein in Human T Cells Inhibits Human Immunodeficiency Virus Replication".

Human Gene Therapy, vol. 5, pp. 79–96, 1994, G.J. Nabel, et al., "A Molecular Genetic Intervention for AIDS–Effects of a Transdominant Form of Rev".

Gene Therapy, vol. 1, pp. 32–37, 1994, J. Liu, et al., "Regulated Expression of a Dominant Negative Form of Rev Improves Resistance to HIV Replication in T Cells".

Proc. Natl. Acad. Sci. USA, vol. 89, pp. 9870–9874, Oct. 1992, Bevec, et al., "Inhibition of Human Immunodeficiency Virus Type 1 Replication in Human T Cells by Retroviral–Mediated Gene Transfer of a Dominant–Negative Rev Trans–Activator".

Cell, vol. 58, pp. 205–214, Jul. 1989, Malim, et al., "Functional Dissection of the HIV–1 Rev Trans–Activator–Derivation of a Trans–Dominant Repressor of Rev Function".

Cell, vol. 59, pp. 113–120, 1989, Trono, et al., "HIV–1 Gag Mutants Can Dominantly Interfere With the Replication of the Wild–Type Virus".

Gene Therapeutics Methods and Applications of Direct Gene Transfer, pp. 193–209, 1994, Yang, et al., "Gene Transfer Via Particle Bombardment: Applications of the Accell Gene Gun".

Nature, vol. 356, pp. 152–154, Mar. 12, 1992, Tang, et al., "Genetic Immunization is a Simple Method for Eliciting an Immune Response".

Trends In Genetics, vol. 10, No. 4, pp. 139–144, Apr. 1994, Gilboa, et al., "Gene Therapy for Infectious Diseases: The AIDS Model".

Human Gene Therapy, vol. 5, pp. 149–150, 1994, Anderson, "Gene Therapy for AIDS".

Annual Review of Immunology, vol. 1, pp. 297–329, 1993, Cournoyer, et al., "Gene Therapy of the Immune System".

Proc. Natl. Acad. Sci. USA, vol. 90, pp. 7889–7893, Aug. 1993, Marasco, et al., "Design, Intracellular Expression, and Activity of a Human Anti–Human Immunodeficiency Virus Type 1 gp120 Single–Chain Antibody".

Proc. Natl. Acad. Sci. USA, vol. 90, pp. 8000–8004, Sep. 1993, Lisziewicz, et al., "Inhibition of Human Immunodeficiency Virus Type 1 Replication by Regulated Expression of a Polymeric Tat Activation Response RNA Decoy as a Strategy for Gene Therapy in AIDS".

Proc. Natl. Acad. Sci. USA, vol. 89, pp. 10802–10806, Nov. 1992, Ojwang, et al., "Inhibition of Human Immunodeficiency Virus Type 1 Expression by a Hairpin Ribozyme".

Proc. Natl. Acad. Sci. USA, vol. 88, pp. 7303–7307, Aug. 1991, Sioud, et al., "Prevention of Human Immunodeficiency Virus Type 1 Integrase Expression in *Escherichia coli* by a Ribozyme".

Trends in Genetics, vol. 9, No. 12, pp. 433–437, Dec. 1993, Vink, et al., "The Human Immunodeficiency Virus Integrase Protein".

PA Pizzo et al (1994) Clinical Infectious Diseases 19: 177–196.

H Collins (Mar. 6, 1993) Philadelphia Inquirer p. A01.

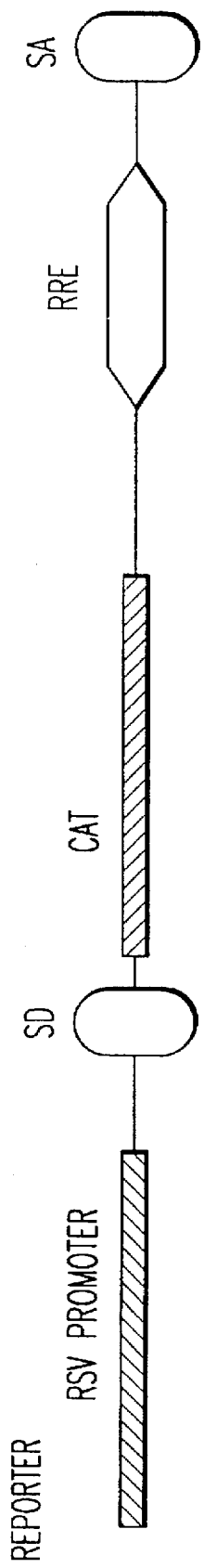
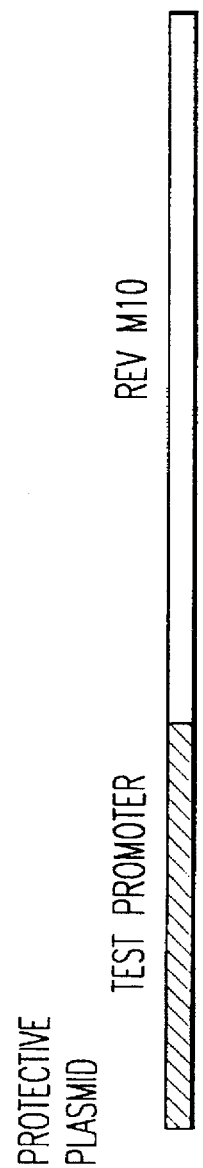
FIG. 1A
FIG. 1B
FIG. 1C

FIG. 11A

RSV tar Rev M10 expression plasmid

| Region | From | To | Description |
|---|---|---|---|
| pBR322 | 1 | 36 | Vector |
| enhancer | 37 | 610 | RSV |
| tar | 611 | 699 | tat responsive element |
| rev m10 | 700 | 1129 | Rev M10 orf |
| poly A | 1243 | | bov.GH |
| promoter | 1993 | 2300 | pSV neo |
| kana res. | 2346 | | pSV2 neo |
| poly A | 3360 | | pSV2neo |
| pUC | 3459 | 5653 | plasmid orf/amp |

Rtrev. Seq Length: 5653  April 8, 1993  14:30  Type: N  Check: 1915

```
  1 GACGGATCGG GAGATCTCCC GATCCCCTAT GGTCGACTCT CAGTACAATC
 51 TGCTCTGATG CCGCATAGTT AAGCCAGTAT CTGCTCCCTG CTTGTGTGTT
```

FIG. 11B

```
101  GGAGGTCGCT  GAGTAGTGCG  CGAGCAAAAT  TTAAGCTACA  ACAAGGCAAG
151  GCTTGACCGA  CAATTGCATG  AAGAATCTGC  TTAGGGTTAG  GCGTTTTGCG
201  CTGCTTCGCG  ATGTACGGGC  CAGATATACG  CGTATCTGAG  GGGACTAGGG
251  TGTGTTTAGG  CGAAAAGCGG  GGCTTCGGTT  GTACGCGGTT  AGGAGTCCCC
301  TCAGGATATA  GTAGTTTCGC  TTTTGCATAG  GGAGGGGAA   ATGTAGTCTT
351  ATGCAATACA  CTTGTAGTCT  TGCAACATGG  TAACGATGAG  TTAGCAACAT
401  GCCTTACAAG  GAGAGAAAAA  GCACCGTGCA  TGCCGATTGG  TGGAAGTAAG
451  GTGGTACGAT  CGTGCCTTAT  TAGGAAGGCA  ACAGACAGGT  CTGACATGGA
501  TTGGACGAAC  CACTGAATTC  CGCATTGCAG  AGATAATTGT  ATTTAAGTGC
551  CTAGCTCGAT  ACAATAAACG  CCATTTGACC  ATTCACCACA  TTGGTGTGCA
601  CCTCCAAGCT  CTGCTTTTTG  CCTGTACTGG  GTCTCTCTGG  TTAGACCAGA
651  TCTGAGCCTG  GGAGCTCTCT  GGCTAGCTAG  GGAACCCACT  GCTTAAGCTC
701  ATGGCAGGAA  GAAGCGGAGA  CAGCGACGAA  GACCTCCTCA  AGGCAGTCAG
751  ACTCATCAAG  TTTCTCTATC  AAAGCAACCC  ACCTCCCAAT  CCCGAGGGA
```

FIG. 11C

```
 801  CCCGACAGGC  CCGAAGGAAT  AGAAGAAGAA  GGTGGAGAGA  GAGACAGAGA
 851  CAGATCCATT  CGATTAGTGA  ACGGATCCTT  AGCACTTATC  TGGGACGATC
 901  TGCGAGCCTG  TGCCTCTTCA  GCTACCACCA  GATCTGAGAC  TTACTCTTGA
 951  TTGTAACGAG  GATTGTGGAA  CTTCTGGGAC  GCAGGGGTG   GGAAGCCCTC
1001  AAATATTGGT  GGAATCTCCT  ACAGTATTGG  AGTCAGGAAC  TAAAGAATAG
1051  TGCTGTTAGC  TTGCTCAATG  CCACAGCTAT  AGCAGTAGCT  GAGGGGACAG
1101  ATAGGGTTAT  AGAAGTAGTA  CAAGAAGCTC  TAGAGCTCGC  TGATCAGCCT
1151  CGACTGTGCC  TTCTAGTTGC  CAGCCATCTG  TTGTTTGCCC  CTCCCCCGTG
1201  CCTTCCTTGA  CCCTGGAAGG  TGCCACTCCC  ACTGTCCTTT  CCTAATAAAA
1251  TGAGGAAATT  GCATCGCATT  GTCTGAGTAG  GTGTCATTCT  ATTCTGGGGG
1301  GTGGGGTGGG  GCAGGACAGC  AAGGGGGAGG  ATTGGGAAGA  CAATAGCAGG
1351  CATGCTGGGG  ATGCGGGTGGG  CTCTATGGCT  TCTGAGGCGG  AAAGAACCAG
1401  CTGGGCTCG   AGGGGGATC   CCCACGCGCC  CGGTAGCGGC  GCATTAAGCG
1451  CGGCGGGTGT  GGTGGTTACG  CGCAGCGTGA  CCGCTACACT  TGCCAGCGCC
```

FIG. 11D

```
1501  CTAGCGCCCG  CTCCTTTCGC  TTTCTTCCCT  TCCTTTCTCG  CCACGTTCGC
1551  CGGCTTTCCC  CGTCAAGCTC  TAAATCGGGG  CATCCCTTTA  GGGTTCCGAT
1601  TTAGTGCTTT  ACGGCACCTC  GACCCCAAAA  AACTTGATTA  GGGTGATGGT
1651  TCACGTAGTG  GGCCATCGCC  CTGATAGACG  GTTTTTCGCC  CTTTGACGTT
1701  GGAGTCCACG  TTCTTTAATA  GTGGACTCTT  GTTCCAAACT  GGAACAACAC
1751  TCAACCCTAT  CTCGGTCTAT  TCTTTTGATT  TATAAGGGAT  TTTGGGATT
1801  TCGGCCTATT  GGTTAAAAAA  TGAGCTGATT  TAACAAAAAT  TTAACGCGAA
1851  TTTTAACAAA  ATATTAACGT  TTACAATTTA  AATATTTGCT  TATACAATCT
1901  TCCTGTTTTT  GGGGCTTTTC  TGATTATCAA  CCGGGGTGGG  TACCGAGCTC
1951  GAATTCTGTG  GAATGTGTGT  CAGTTAGGGT  GTGGAAAGTC  CCCAGGCTCC
2001  CCAGGCAGGC  AGAAGTATGC  AAAGCATGCA  TCTCAATTAG  TCAGCAACCA
2051  GGTGTGGAAA  GTCCCCAGGC  TCCCCAGCAG  GCAGAAGTAT  GCAAAGCATG
2101  CATCTCAATT  AGTCAGCAAC  CATAGTCCCG  CCCCTAACTC  CGCCCATCCC
2151  GCCCCTAACT  CCGCCCAGTT  CCGCCCATTC  TCCGCCCCAT  GGCTGACTAA
```

FIG. 11E

```
2201  TTTTTTTTAT  TTATGSAGAG  GCCGAGGCCG  CCTCGGCCTC  TGAGCTATTC
2251  CAGAAGTAGT  GAGGAGGCTT  TTTTGGAGGC  CTAGGCTTTT  GCAAAAAGCT
2301  CCCGGGAGCT  TGGATATCCA  TTTTCGGATC  TGATCAAGAG  ACAGGATGAG
2351  GATCGTTTCG  CATGATTGAA  CAAGATGGAT  TGCACGCAGG  TTCTCCGGCC
2401  GCTTGGGTGG  AGAGGCTATT  CGGCTATGAC  TGGGCACAAC  AGACAATCGG
2451  CTGCTCTGAT  GCCGCCGTGT  TCCGGCTGTC  AGCGCAGGGG  CGCCCGGTTC
2501  TTTTTGTCAA  GACCGACCTG  TCCGGTGCCC  TGAATGAACT  GCAGGACGAG
2551  GCAGCGCGGC  TATCGTGGCT  GGCCACGACG  GGCGTTCCTT  GCGCAGCTGT
2601  GCTCGACGTT  GTCACTGAAG  CGGGAAGGGA  CTGGCTGCTA  TTGGGCGAAG
2651  TGCCGGGGCA  GGATCTCCTG  TCATCTCACC  TTGCTCCTGC  CGAGAAAGTA
2701  TCCATCATGG  CTGATGCAAT  GCGGCGGCTG  CATACGCTTG  ATCCGGCTAC
2751  CTGCCCATTC  GACCACCAAG  CGAAACATCG  CATCGAGCGA  GCACGTACTC
2801  GGATGGAAGC  CGGTCTTGTC  GATCAGGATG  ATCTGGACGA  AGAGCATCAG
2851  GGGCTCGCGC  CAGCCGAACT  GTTCGCCAGG  CTCAAGGCGC  GCATGCCCGA
```

FIG. 11F

```
2901  CGGGGAGGAT  CTCGTCGTGA  CCCATGGCGA  TGCCTGCTTG  CCGAATATCA
2951  TGGTGGAAAA  TGGCCGCTTT  TCTGGATTCA  TCGACTGTGG  CCGGCTGGGT
3001  GTGGCGGACC  GCTATCAGGA  CATAGCGTTG  GCTACCCGTG  ATATTGCTGA
3051  AGAGCTTGGC  GGCGAATGGG  CTGACCGCTT  CCTCGTGCTT  TACGGTATCG
3101  CCGCTCCCGA  TTCGCAGCGC  ATCGCCTTCT  ATCGCCTTCT  TGACGAGTTC
3151  TTCTGAGCGG  GACTCTGGGG  TTCGAAATGA  CCGACCAAGC  GACGCCCAAC
3201  CTGCCATCAC  GAGATTTCGA  TTCCACCGCC  GCCTTCTATG  AAAGGTTGGG
3251  CTTCGGAATC  GTTTTCCGGG  ACGCCGGCTG  GATGATCCTC  CAGCGCGGGG
3301  ATCTCATGCT  GGAGTTCTTC  GCCCACCCCA  ACTTGTTTAT  TGCAGCTTAT
3351  AATGGTTACA  AATAAAGCAA  TAGCATCACA  AATTTCACAA  ATAAAGCATT
3401  TTTTTCACTG  CATTCTAGTT  GTGGTTTGTC  CAAACTCATC  AATGTATCTT
3451  ATCATGTCTG  GATCCCGTCG  ACCTCGAGAG  CTTGGCGTAA  TCATGGTCAT
3501  AGCTGTTTCC  TGTGTGAAAT  TGTTATCCGC  TCACAATTCC  ACACAACATA
3551  CGAGCCGGAA  GCATAAAGTG  TAAAGCCTGG  GGTGCCTAAT  GAGTGAGCTA
```

FIG. 11G

```
3601  ACTCACATTA  ATTGCGTTGC  GCTCACTGCC  CGCTTTCCAG  TCGGGAAACC
3651  TGTCGTGCCA  GCTGCATTAA  TGAATCGGCC  AACGCGCGGG  GAGAGGCGGT
3701  TTGCGTATTG  GGCGCTCTTC  CGCTTCCCTC  CTCACTGACT  CGCTGCGCTC
3751  GGTCGTTCGG  CTGCGGCGAG  CGGTATCAGC  TCACTCAAAG  GCGGTAATAC
3801  GGTTATCCAC  AGAATCAGGG  GATAACGCAG  GAAAGAACAT  GTGAGCAAAA
3851  GGCCAGCAAA  AGGCCAGGAA  CCGTAAAAAG  GCCGCGTTGC  TGGCGTTTTT
3901  CCATAGGCTC  CGCCCCCCTG  ACGAGCATCA  CAAAAATCGA  CGCTCAAGTC
3951  AGAGGTGGCG  AAACCCGACA  GGACTATAAA  GATACCAGGC  GTTTCCCCCT
4001  GGAAGCTCCC  TCGTGCGCTC  TCCTGTTCCG  ACCCTGCCGC  TTACCGGATA
4051  CCTGTCCGCC  TTTCTCCCTT  CGGGAAGCGT  GGCGCTTTCT  CAATGCTCAC
4101  GCTGTAGGTA  TCTCAGTTCG  GTGTAGGTCG  TTCGCTCCAA  GCTGGGCTGT
4151  GTGCACGAAC  CCCCCGTTCA  GCCCGACCGC  TGCGCCTTAT  CCGGTAACTA
4201  TCGTCTTGAG  TCCAACCCGG  TAAGACACGA  CTTATCGCCA  CTGGCAGCAG
4251  CCACTGGTAA  CAGGATTAGC  AGAGCGAGGT  ATGTAGGCGG  TGCTACAGAG
```

FIG. 11H

```
4301  TTCTTGAAGT  GGTGGCCTAA  CTACGGCTAC  ACTAGAAGGA  CAGTATTTGG
4351  TATCTGCGCT  CTGCTGAAGC  CAGTTACCTT  CGGAAAAAGA  GTTGGTAGCT
4401  CTTGATCCGG  CAAACAAACC  ACCGCTGGTA  GCGGTGGTTT  TTTTGTTTGC
4451  AAGCAGCAGA  TTACGCGCAG  AAAAAAAGGA  TCTCAAGAAG  ATCCTTTGAT
4501  CTTTTCTACG  GGGTCTGACG  CTCAGTGGAA  CGAAAACTCA  CGTTAAGGGA
4551  TTTTGGTCAT  GAGATTATCA  AAAAGGATCT  TCACCTAGAT  CCTTTTAAAT
4601  TAAAAATGAA  GTTTTAAATC  AATCTAAAGT  ATATATGAGT  AAACTTGGTC
4651  TGACAGTTAC  CAATGCTTAA  TCAGTGAGGC  ACCTATCTCA  GCGATCTGTC
4701  TATTTCGTTC  ATCCATAGTT  GCCTGACTCC  CCGTCGTGTA  GATAACTACG
4751  ATACGGGAGG  GCTTACCATC  TGGCCCCAGT  GCTGCAATGA  TACCGCGAGA
4801  CCCACGCTCA  CCGGCTCCAG  ATTTATCAGC  AATAAACCAG  CCAGCCGGAA
4851  GGGCCGAGCG  CAGAAGTGGT  CCTGCAACTT  TATCCGCCTC  CATCCAGTCT
4901  ATTAATTGTT  GCCGGGAAGC  TAGAGTAAGT  AGTTCGCCAG  TTAATAGTTT
4951  GCGCAACGTT  GTTGCCATTG  CTACAGGCAT  CGTGGTGTCA  CGCTCGTCGT
```

FIG. 11I

```
5001 TTGGTATGGC TTCATTCAGC TCCGGTTCCC AACGATCAAG GCGAGTTACA
5051 TGATCCCCCA TGTTGTGCAA AAAAGCGGTT AGCTCCTTCG GTCCTCCGAT
5101 CGTTGTCAGA AGTAAGTTGG CCGCAGTGTT ATCACTCATG GTTATGGCAG
5151 CACTGCATAA TTCTCTTACT GTCATGCCAT CCGTAAGATG CTTTTCTGTG
5201 ACTGGTGAGT ACTCAACCAA GTCATTCTGA GAATAGTGTA TGCGGCGACC
5251 GAGTTGCTCT TGCCCGGCGT CAATACGGGA TAATACCGCG CCACATAGCA
5301 GAACTTTAAA AGTGCTCATC ATTGGAAAAC GTTCTTCGGG GCGAAAACTC
5351 TCAAGGATCT TACCGCTGTT GAGATCCAGT TCGATGTAAC CCACTCGTGC
5401 ACCCAACTGA TCTTCAGCAT CTTTTACTTT CACCAGCGTT TCTGGGTGAG
5451 CAAAAACAGG AAGGCAAAAT GCCGCAAAAA AGGGAATAAG GGCGACACGG
5501 AAATGTTGAA TACTCATACT CTTCCTTTTT CAATATTATT GAAGCATTTA
5551 TCAGGGTTAT TGTCTCATGA GCGGATACAT ATTTGAATGT ATTTAGAAAA
5601 ATAAACAAAT AGGGGTTCCG CGCACATTTC CCCGAAAAGT GCCACCTGAC
5651 GTC
```

INTRODUCTION OF HIV-PROTECTIVE GENES INTO CELLS BY PARTICLE-MEDIATED GENE TRANSFER

The present invention was made with the assistance of United States Government funds. The United States Government may have some rights in the invention.

BACKGROUND OF THE INVENTION

1. Field of the Invention

The present invention relates to a method for introducing a gene into a patient's T cells, monocytes, macrophages, dendrites, or hematopoietic stem cells, and to a method for introducing HIV protective genes into a patient's cells by particle-mediated gene transfer and reagents and kits useful in such methods.

2. Discussion of the Background

Infection by human immunodeficiency Virus (HIV) leads to progressive depletion of $CD4^+$ T cells which causes an acquired immunodeficiency syndrome (AIDS). Over the past decade, AIDS infection has achieved epidemic proportions. Despite considerable progress in understanding and diagnosing this disease, it has remained refractory to treatment. There are currently no effective means to vaccinate susceptible individuals or to treat infected patients. Infection by the human immunodeficiency virus is typically characterized by an asymptomatic, or latent, phase of the disease. During this time, patients may not exhibit signs of immunodeficiency but nonetheless synthesize virus which progressively depletes $CD4^+$ T cells and is infectious. It is currently estimated that there are over one million seropositive cases with latent HIV infection in the United States today. These individuals, for whom there are no known effective treatments, are likely to progress and succumb to this disease.

For these individuals, a major therapeutic goal is to prolong the latent phase of HIV infection. A major interest has been to define the molecular basis of HIV gene activation in T lymphocytes. The activation of HIV gene expression is controlled by a cellular transcription factor, NF-κB (G. Nabel, D. Baltimore, *Nature*, vol. 326, p. 711 (1987)). This transcription factor is inactive in resting T cells but is stimulated following cell activation and induces viral transcription. In addition to NF-κB, there are essential viral genes which also appear to regulate the transition from latent to active infection. An important viral regulatory protein in this process is Rev, an 19 kDa nuclear protein which controls export of viral RNA from the nucleus to the cytoplasm of infected cells.

Viral replication is critically dependent on the interaction of viral gene products with host cell factors. Because viruses are intimately associated with their host cells, it has been difficult to selectively interfere with replication in vivo. Successful antiviral approaches have selectively targeted viral gene products. For example, the treatment of herpes simplex virus (HSV) infection has taken advantage of the ability of a viral gene, thymidine kinase, to modify a drug which is toxic to the host cell. This approach led to the development of guanosine analogues, including acyclovir and ganciclovir (K. O. Smith, K. S. Galloway, W. L. Kennell, K. K. Ogilvie, B. K. Radatus, *Antimicrob. Agents Chemother.*, vol. 22, p. 55 (1982); A. K. Field, M. E. Davies, C. DeWitt, H. C. Perry, R. Liou, et al, *Proc. Natl. Acad. Sci.*, USA, vol. 80, p. 4139 (1983); D. F. Smee, J. C. Martin, J. P. Verheyden, T. R. Matthews, *Antimicrob. Agents Chemother.*, vol. 23, p. 676 (1983)), which are converted to DNA chain terminators only in HSV infected cells.

In HIV infection, traditional pharmaceutical targeting has thus far provided limited benefits. Although AZT has relative selectivity for viral reverse transcriptase, its toxic effect on host cell function and its low therapeutic index has provided limited protection against the progression of AIDS.

Although drug discovery has led to the identification of additional anti-viral drugs, the high rate of virus mutation has led to the generation of resistant viral mutants. More recently, as molecular biological studies have advanced, it has become possible to use recombinant genes to interfere with HIV gene expression. Several approaches have been used to exploit gene transfer to inhibit viral replication. These include anti-sense RNA (H. Weintraub J. G. Izant, R. M. Harland, *Trends Genet.*, vol. 2, p. 22 (1985); J. P. Green, O. Pines, M. Inouye, *Ann. Rev. Biochem*, vol. 55, p. 569 (1986); A. R. van der Krol, J. N. M. Mol, A. R. Stuitjie, *BioTech*, vol. 6, p. 958 (1988)), catalytic RNA, or ribozymes (J. Hasseloff, W. L. Gerlach, *Nature*, vol. 334, p. 585 (1988); M. Cotton, M. L. Birnstiel, *EMBO J*, vol. 8, p. 3861 (1989); N. Sarver, E. M. Cantin, P. S. Chang, J. A. Zaia, P. A. Ladne, et al, *Science*, vol. 247, p. 1222 (1990); B. A. Sullenger, T. C. Lee, C. A. Smith, G. E. Ungers, E. Gilboa, *Mol. Cell. Biol.*, vol. 10, p. 6512 (1990)), and RNA analogs or decoys (B. A. Sullenger, H. F. Gallardo, G. E. Ungers, E. Gilboa, *Cell*, vol. 63, p. 601 (1990)). The gene transfer approach to targeting viral nucleic acid is complicated by problems of delivering the antiviral gene to the appropriate compartment of the cell, and by the ability to obtain catalytic activity in vivo. These approaches have thus far have not been successful.

The concept of dominant negative-inhibition was initially described in yeast genetic systems (I. Herskowitz, *Nature*, vol. 329, p. 219 (1987)). It was subsequently demonstrated that anti-viral effects could be conferred on cells susceptible to infection by herpesvirus. Using the herpesvirus VP16 transactivator, mutant proteins lacking the transactivation domain of this protein were generated which could interfere with viral replication (A. D. Friedman, S. J. Triezenberg, S. L. McKnight, *Nature*, vol. 335, p. 452 (1988)). For HIV, several potential transdominant proteins have been defined which have been successful for inhibiting viral replication in transient transfection systems. Among these are the Rev transdominant protein (M. H. Malim, S. Bohnlein, J. Hauber, B. R. Cullen, *Cell*, vol. 58, p. 205 (1989)) and viral group-specific antigens (GAG). Recent success in protecting cells from HIV infection using TAR analogs has provided additional evidence that it is possible to render cells resistant to HIV infection (B. A. Sullenger, H. F. Gallardo, G. E. Ungers, E. Gilboa, *Cell*, vol. 63, p. 601 (1990)) through recombinant gene products.

Previous gene therapy attempts to protect cells from HIV infection have focused upon a viral vector delivery system, because, prior to the present invention, no method other than viral transfection was thought to be useful for introducing a gene into a patient's T cells. In other words, T cells are resistant to the uptake and stable expression of foreign DNA. However, a major concern regarding the utilization of viral vector delivery systems is the potential for small quantities of replication-competent virus to remain undetected in large production lots intended for clinical use. Since it is not possible to test the entire lot, quantities below the detection limits of the assay could be introduced into the patient. Given the underlying immunodeficiency of these patients, the potential to establish replication-competent virus in the host would be increased. Although proper testing of retroviral vector batches makes this possibility less likely, it remains a risk in this procedure. The use of a nonviral vector which is unable to replicate provides an alternative to this approach which might improve its safety. A variety of approaches have been attempted to introduce genes into T cells, but most are limited by low transduction efficiencies, transient expression, and the general resistance of T cells to the uptake of recombinant DNA.

Thus, the treatment of HIV infection by gene therapy remains elusive. Thus, there remains a need for a method of treating HIV infection. In particular, there remains a need for a method for introducing an HIV-protective gene into a patient's T cells, monocytes, macrophages, or hematopoietic stem cells. There also remains a need for reagents and kits for carrying out such a method.

SUMMARY OF THE INVENTION

Accordingly, it is one object of the present invention to provide novel methods for treating HIV infection.

It is another object of the present invention to provide a method for prolonging the latent phase of HIV infection in a patient infected with HIV.

It is another object of the present invention to provide a method for delaying the onset of AIDS in a patient infected with HIV.

It is another object of the present invention to provide a method for introducing a foreign gene into a patient's T cells, monocytes, macrophages, hematopoietic stem cells, or dendrites.

It is another object of the present invention to provide a method for introducing an HIV protective gene into a patient's T cells, monocytes, macrophages, hematopoietic stem cells, or dendrites.

It is another object of the present invention to provide a method for achieving stable expression of a foreign gene in a patient's T cells, monocytes, macrophages, hematopoietic stem cells, or dendrites.

It is another object of the present invention to provide a method for achieving stable expression of an HIV-protective gene in a patient's cells.

It is another object of the present invention to provide a method for introducing an HIV-protective gene into non-activated cells.

It is another object of the present invention to provide novel reagents useful in such a method.

It is another object of the present invention to provide novel kits for carrying out such a method.

These another objects, which will become apparent during the following detailed description, have been achieved by the inventors' discovery that foreign genes may be stably introduced into a patient's T cells, monocytes, macrophages, hematopoietic stem cells, and dendrites and that HIV protective genes may be successfully introduced into a patient's cells by particle-mediated gene transfer.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 1 provides schematic diagrams of Rev-responsive CAT reporter RSV-CAT-RRE, RSV-Rev and the different promoter protective plasmids. SD, splice donor; SA, splice acceptor; RRE, Re-responsive element;

FIG. 11A–11I show the sequence (SEQ ID NO: 1) of the RSV tar Rev M10 expression plasmid (pRSVtRevM10);

(a) Time course of HIV$^{BRU}$ infection of an individual group of Rev M10 and ΔRev M10 transduced PBLs.

Figure 13A:
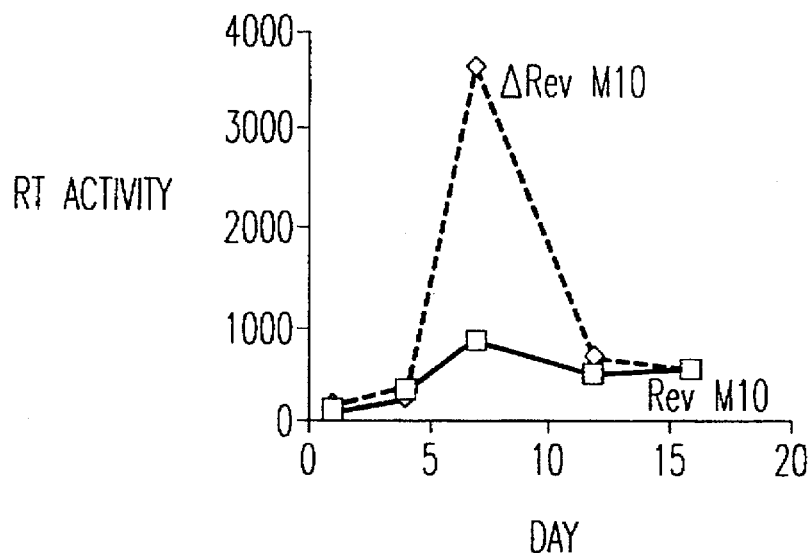
Figure 13B:
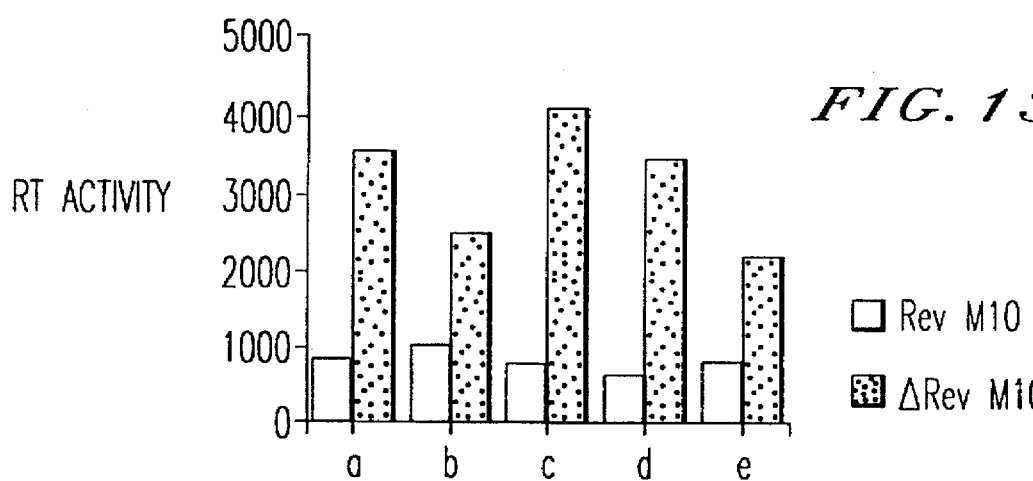

(b) PBLs from different donors were stimulated via PHA/IL-2 (groups a–c) or anti-CD3/IL-2 (groups d and e) as in the Examples. Following retroviral transduction with Rev M10 and ΔRev M10, and G-418 selection for 1 week, cells were challenged with HIV. RT activity shown for each group is for 7–8 days post-HIV infection;

FIGS. 13a and 13b show the results of the challenge of Rev M10/ΔRev M10 retrovirally transduced human PBLs with a clinical isolate of HIV, HIV$^{CLIN}$. PBLs were stimulated, transduced, and selected in G-418 for 1 week as described in the Examples. Cells were then challenged with HIV at a MOI between 0.02 and 0.05.

(a) Time course of HIV$^{CLIN}$ infection of an individual group of Rev M10 and ΔRev M10 transduced PBLs.

Figure 14A:
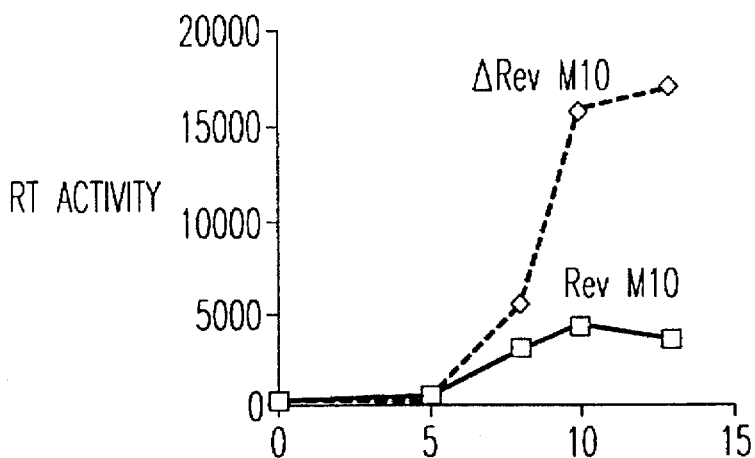
Figure 14B:
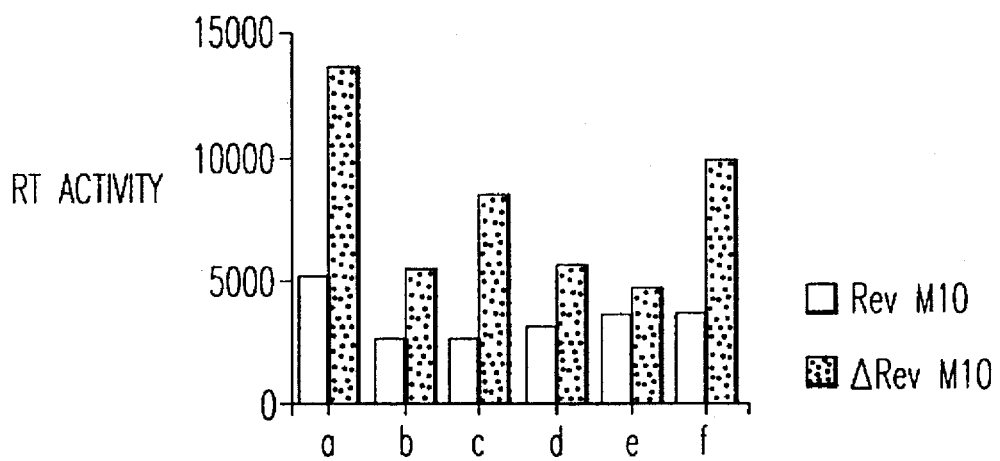

(b) PBLs from different donors were stimulated via PHA/IL-2 (groups a–c) or anti-CD3/IL-2 (groups d and e) as described in the Examples. Following retroviral transduction with Rev M10 and ΔRev M10, and G-418 selection for 1 week, cells were challenged with HIV. RT activity shown for each group is for 7–8 days post-HIV infection;

FIGS. 14a and 14b show the results of the challenge of particle-mediated Rev M10/ΔRev M10 transduced human PBLs with HIV$^{BRU}$. Freshly isolated PBLs were stimulated with anti-CD3/IL-2 as described in the Examples. After particle-mediated transduction and selection in G-418 for up to 8 days, cells were challenged with HIV$^{BRU}$ at a MOI of between 0.02 and 0.05.

(a) Time course of HIV infection of an individual group set of Rev M10 and ΔRev M10 transduced PBLs.

Figure 15A:
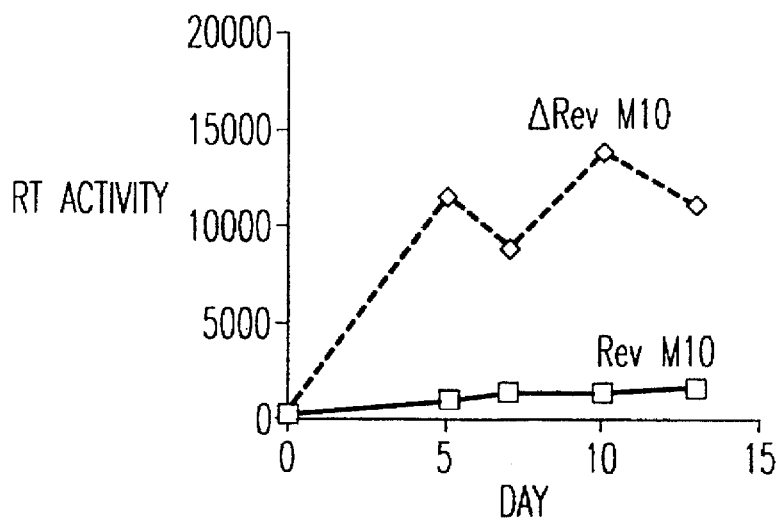
Figure 15B:
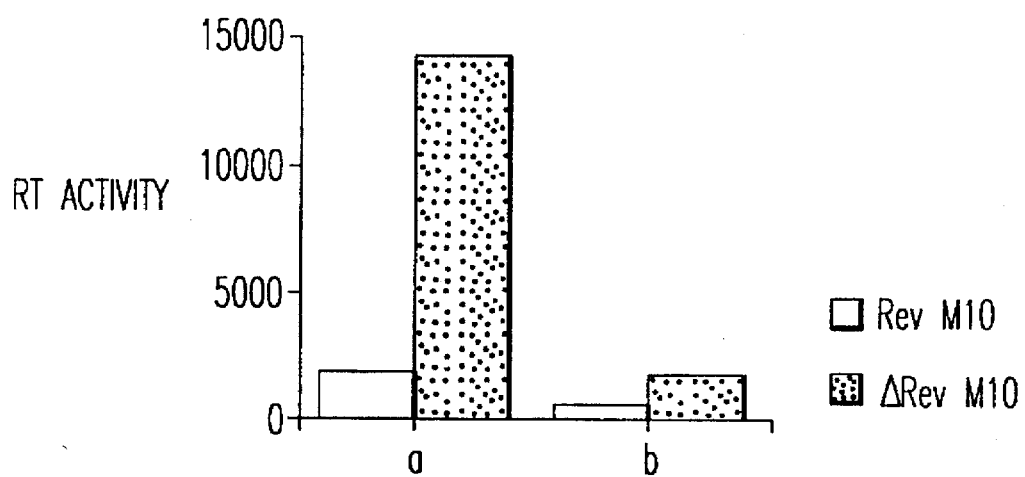

(b) Different experimental sets (a–h) of independently transduced PBLs from various donors were challenged with HIV$^{BRU}$. RT activity is 7–8 days post-HIV infection;

FIGS. 15a and 15b show the results of the challenge of particle-mediated Rev M10/ΔRev M10 transduced human PBLs with 2 clinical isolates of HIV. Freshly isolated PBLs were stimulated with anti-CD3/IL-2 as described in the Examples. After particle-mediated transduction and selection in G-418 for up to 8 days, cells were challenged with HIV$^{CLIN}$ at a MOI of between 0.02 and 0.05.

(a) Time course of HIV infection of an individual group set of Rev M10 and ΔRev M10 transduced PBLs.

Figure 16:
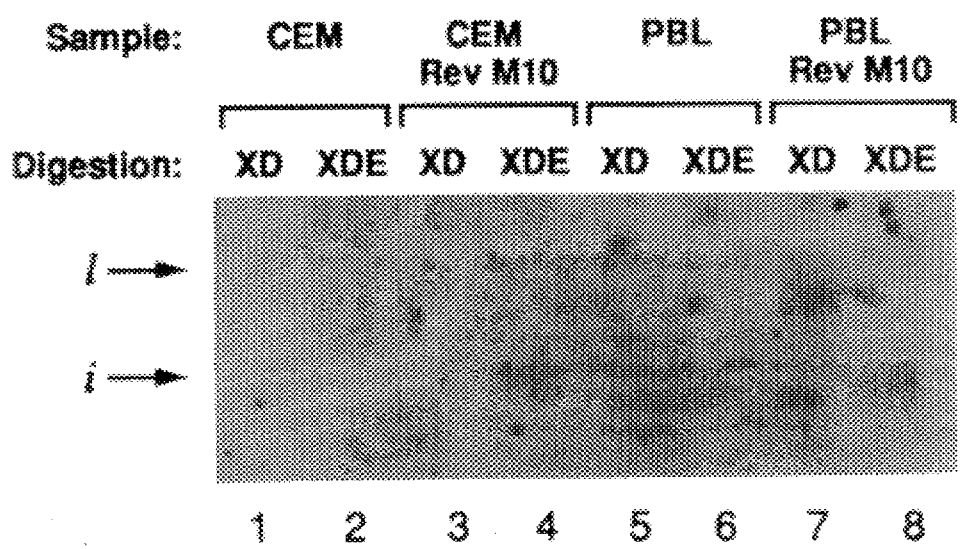

(b) Two groups (a and b) of independently transduced PBLs were challenged with 2 different clinical isolates of HIV-1. RT activity is 7–8 days post-HIV infection; and FIG. 16 illustrates the results of a Southern blot analysis of T leukemia and human PBL transduced with Rev M10 by particle-mediated gene transfer. DNA samples were prepared and digested with XbaI and DraIII (XD) or XbaI, DraIII, and EcoRI(XDE) to detect linearized (l) or integrated (i) forms of the plasmid. CEM (lanes 1–4) or PBL (lanes 5–8), untransduced or transduced as indicated, were probed (see Examples).

DETAILED DESCRIPTION OF THE PREFERRED EMBODIMENTS

Thus, in a first embodiment, the present invention provides a method for introducing a foreign gene into a patient's T cells, monocytes, macrophages, hematopoietic stem cells, or dendrites. In the present method, the foreign gene is introduced into cells by particle-mediated gene transfer. Particle-mediated gene transfer is described in U.S. Pat. Nos. 5,015,580 and 5,120,657, which are incorporated herein by reference. Additional details of pareticle-mediated gene transfer are taught in J. K. Burkholder, et al, *J. Immunological Methods*, vol. 165, pp. 149–56 (1993); N. S. Yang, et al, *Proc. Natl. Acad. Sci. USA*, vol. 87, pp. 9568–72 (1990); S. Jiao, et al, *Bio/Technology*, vol. 11, pp. 497–502 (1993); T. A. Thompson, et al, *In Vitro Cell. Dev. Biol.*, vol. 29A, pp. 167–170 (1993); N. -S. Yang, et al, *Critical Rev. in Biotechnology*, vol. 12, pp. 335–356 (1992); L. Cheng, et al, *Proc. Natl. Acad. Sci. USA*, vol. 90, pp. 4455–4459 (1993); N. -S. Yang, et al, *Proc. Natl. Acad. Sci. USA*, vol. 87, pp. 9598–9572 (1990), all of which are incorporated herein by reference.

In particle mediated gene transfer, the gene to be introduced into the cell is coated on a small inert particle which is then forced through the cell, thus introducing the gene into the cell. The inert particle may be made of any inert material such as an inert metal (gold, silver, platinum, tungsten etc.) or inert plastic (polystyrene, polypropylene, polycarbonate, etc.). Preferably, the particle is made of gold, platinum, or tungsten. Most preferably, the particle is gold. Suitably, the particle is spherical and has a diameter of 0.5 to 5 microns, preferably 1 to 3 microns.

In the present invention, the foreign gene may be any gene which is desired to be introduced into a patient's T cells, monocytes, macrophages, hematopoietic stem cells, or dendrites. Preferably, the gene is a HIV-protective gene. The HIV-protective gene may be any gene which will confer an HIV-protective effect on the cell. Examples of such materials include dominant-negative inhibition genes, ribozymes, antisense genes, etc. Preferably, the HIV-protective gene is a dominant-negative inhibition gene, such as Rev M10, an inhibitory integrase or gag gene (Trono, D., et al, *Cell*, vol. 59, pp. 113–120 (1989)). In a particularly preferred embodiment, the protective gene is Rev M10.

The protective gene may be introduced in any suitable form including, a linearized plasmid, a circular plasmid, a plasmid capable of replication, an episome, RNA, etc. Preferably, the gene is contained in a plasmid. In a particularly preferred embodiment, the gene is contained in a linearized plasmid.

In a particularly preferred embodiment, the HIV-protective gene is contained in a plasmid and is downstream from a promoter. Suitable promoters include the RSV promoter (Liu, J., et al, *Gene Ther.*, vol. 1, pp. 32–37 (1994); and the CD4 enhancer/promoter (Sawada, S., et al, *Mol. Cell. Biol.*, vol 11, pp. 5506–5515 (1991)). Preferably the promoter is the RSV promoter. More preferably, the HIV-protective gene is downstream from the sequence of TAR from −18 to −72 of the HIV promoter. Most preferably, the HIV-protective gene is immediately downstream from the sequence TAR from −18 to −72 of the HIV promoter, which is in turn immediately downstream from the RSV promoter.

The plasmid which contains the HIV-protective gene may also contain a selectable marker so that the cells which contain the plasmid can be selectively expanded. Examples of suitable selectable markers include, neo, gpt, mdr, hygro or dhfr. Preferably, the selectable marker is neo.

The gene to be introduced into the cell may be coated on the particle by conventional methods. For example, the DNA sequence containing the protective gene prepared in the form suitable for gene introduction can be simply dried onto naked gold or tungsten pellets. However, DNA molecules in such a form may have a relatively short period of stability and may tend to degrade rather rapidly due to chemical reactions with the metallic or oxide substrate of the particle itself. Thus, if the carrier particles are first coated with an encapsulating agent, the DNA strands have greatly improved stability and do not degrade significantly even over a time period of several weeks. A suitable encapsulating agent is polylysine (molecular weight 200,000) which can be applied to the carrier particles before the DNA molecules are applied. Other encapsulating agents, polymeric or otherwise, may also be useful as similar encapsulating agents, including spermidine. The polylysine is applied to the particles by rinsing the gold particles in a solution of 0.02% polylysine and then air drying or heat drying the particles thus coated. Once the metallic particles coated with polylysine were properly dried, DNA strands are then loaded onto the particles.

The DNA is loaded onto the particles at a rate of between 3 and 30 micrograms of DNA per milligram of gold bead spheres. To 100 micrograms of DNA and 30 milligrams of 1–3 micron gold spheres are sequentially added 20 µl of 0.1M spermidine, and then 50 microliters of 2.5M $CaCl_2$ to provide a fine calcium precipitate which forms as the solution is dried. The precipitate carries the DNA with it onto the beads. Once the beads and the spermidine and calcium chloride solution are mixed with the DNA, the suspension is washed with ethanol and dried. The optimal ratio of DNA to gold is 5 µg DNA (5 µl) to 3 mg gold particles (50 µl). Once dried the precipitate is immediately resuspended in 100% ethanol for the process of placing the particles onto the carrier sheet.

A preferred procedure begins with 3 milligrams of 1.0 to 3 microns gold beads (a microcrystalline gold) suspended in 50 microliters of water. This is then mixed with 5 micrograms (5 µl) of DNA in up to 100 microliters of water. Then 20 microliters of 0.1M spermidine (free base) is mixed and to this mixture is then added 50 microliters of 2.5M calcium chloride while mixing. The suspension is then gently spun down after which the supernatant is discarded. The solids are then resuspended in 140 µl of 70% ethanol and spundown. The supernatant is discarded and the solids are resuspended in 140 µl of pure ethanol and centrifuged. The liquid is discarded. The resulting solids are then placed on the microcarrier and desicated and dried.

Once the particles coated with the DNA containing the HIV-protective gene have been prepared, they may then be used to introduce the gene into a patient's cells using the method and apparatus described in U.S. Pat. Nos. 5,015,580 and 5,120,657, which are incorporated herein by reference. A preferred apparatus is Biolistics, PDS-1000/He System, Biorad Laboratories, Hercules, Calif.

The cells into which the HIV-protective gene is introduced are those cells susceptable to HIV infection or cells which mature into cells susceptable to HIV infection. Thus, the HIV-protective gene is introduced into T cells, monocytes, macrophages, hematopoietic stem cells which give rise of T cells or macrophages, or dendrites. When introducing the protective gene into T cells, a sample of a patient's T cells is first isolated by conventional methods, such as by Ficoll-Hypaque separation.

Typically, the HIV-protective gene is introduced into $10^9$ to $10^{13}$, preferably $10^{10}$ to $10^{11}$ T cells at a time. Usually, the efficiency of the introduction of the protective gene is 1 to 10%. Thus, when a batch of $10^{10}$ to $10^{11}$ T cells is treated as described above, about $10^9$ to $10^{10}$ T cells containing the HIV-protective gene will be obtained. After the introduction of the HIV-protective gene is complete, the T cells are then reintroduced into the patient by conventional techniques such as described in Rosenberg, S. A., et al, *N. Eng. J. Med.*, vol. 323, pp. 570–578 (1990) which is incorporated herein by reference.

It is preferred that the HIV-protective gene be introduced into from 0.1 to 30%, preferably from 1 to 15%, of the patient's T cells. Thus, it will be typically necessary to repeat the procedure described above from 1 to 10, preferably from 2 to 5 times. In other words, it will be necessary to treat from 1 to 10, preferably 2 to 5 batches of T cells. These batch treatments usually take from 1 to 120 hours and typically are spaced apart by 2 to 24 hours, preferably 4 to 16 hours.

Moreover, since the lifetime of a T cell is typically about 5 days to 1 year, it may be necessary to carry out booster treatments to replenish the T cells carrying the HIV-protective gene as those prepared in the initial treatment die. Such booster treatments are usually performed 0.1 to 3 years, preferably 6 to 12 months, after the initial group of batch treatments.

Alternatively, the cells containing the HIV-protective gene may be expanded, e.g., in the presence of IL-2, so that fewer batches need to be processed. In a preferred embodiment, this expansion is carried out in a manner which results in the selective expansion of those cells into which the HIV-protective gene has been introduced. For example, when the DNA introduced also contains a selectable marker such as neo, expansion in the presence of G-418 will result in the selective expansion of those cells containing the HIV-protective gene.

Alternatively, selection of genetically modified HIV-protected cells may occur within the patient, either by protection from viral lysis which would otherwise lyse those cells or by administration of cytokines, e.g. IL-2, which would allow their amplication in vivo.

In an alternative embodiment, the HIV-protective gene is introduced into hematopoietic stem cells which mature into T cells. In this way, it is possible to obviate the need for booster treatments. This will also facilitate gene transfer into the monocyte/macrophage lineage and central nervous system. Hematopoietic stem cells can be isolated and expanded as described in U.S. Pat. No. 5,087,570 and S. Siena et al., *Blood*, vol. 65, pp. 655–662 (1985), which are incorporated herein by reference. Preferably, the stem cells are isolated from a sample of bone marrow. Once the stem cells have been isolated and expanded, the HIV-protective gene may be introduced using the same methods and apparatus described above.

In a preferred embodiment, the particle-mediated gene transfer is carried out at high cell densities. For example, PBL or T cells which have been cultured for a few days or freshly isolated PBL or T cells are harvested, centrifuged at about 300 g for about 5 minutes and resuspended in growth medium (e.g., RPMI) with serum at a cell density of 1 to 5 million cells per 10 µl. Then about 5 µl to 20 µl of the cell suspension is evenly spread onto a surface area of about 3 $cm^2$, and this suspension is used as the target.

After the HIV-protective gene has been introduced into the stem cells, the stem cells are then reintroduced to the patient using conventional techniques. In this embodiment, it is possible to provide lifelong protection without the need for booster treatments.

A particular advantage of the present method is the surprising discovery that particle-mediated gene transfer using a linearized plasmid results in stable incorporation of the foreign gene as evidenced by Southern blotting experiments. This stable incorporation of a HIV-protective gene provides a number of advantages. First, stable incorporation of the HIV-protective gene in stem cells means that the gene will be passed on to the progeny, conferring life-long protection. Second, stable incorporation in T cells means that upon expansion of and proliferation of the T cells the gene will be incorporated into memory cells.

Although, the particle-mediated gene transfer into T cells may be carried out without T cell stimulation, optimal gene transfer currently requires T cell stimulation. Suitably, the T cells are stimulated with an agent such as PHA, OKT3 monoclonal antibody, IL-2, or CD28 antibody. Suitably, the stimulation is carried out for a time of 1 min to 120 hours, preferably 4 to 72 hours, prior to gene transfer. In a preferred embodiment, the prestimulated T cells are maintained in the absence of a stimulating agent for a time of 4 to 96 hours, preferably 24 to 72 hours, immediately prior to gene transfer. In a particularly preferred embodiment, the T cells are stimulated after gene transfer. The same types of stimulating agents described above may also be used for post-gene-transfer stimulation. The post-gene-transfer stimulation is usually carried out 0 to 120 hours, preferably 15 minutes to 4 hours, after gene transfer and for a time of 8 to 120 hours, preferably 24 to 72 hours. The amount of stimulating agent used will depend on the exact identity of the stimulating agent. However, the selection of the amount of stimulating agent is well within the abilities of the skilled artisan. For PHA, good results are achieved using a concentration of 1 to 5 µg/ml, for OKT3 monoclonal antibody, good results are achieved with 0.1 to 10 µg/ml, and with IL-2 good results are achieved with 1 to 100 U/ml, and with 0.1 to 10 µg/ml of anti-CD28. These agents can be used together or in various combinations, e.g., αCD3+IL-2 or αCD3+αCD28.

T cell stimulation may be accompanied by activation of endogenous provirus. Thus, in a preferred embodiment, T cell stimulation is carried out in the presence of a HIV-1 antiviral inhibitor. Preferred inhibitors include zelaviridine (Richman, D., et al, *Proc. Natl. Acad. Sci. USA*, vol. 88, pp. 11241–11245 (1991)), nevirapine (Romero, D. L., et al, *Proc. Natl. Acad. Sci. USA*, VOL. 88, pp. 8806–8810 (1991)), and a CD4 domain Pseudomonas aeruginosa exotoxin A (CD4-PE40) (V. K. Chaudhary, et al, *Nature*, vol. 335, pp. 369–372, (1988)). Preferably, one of zelaviridine and nevirapine is used in conjunction with CD4-PE40. Suitably, the concentration of zelaviridine or nevirapine is 0.01 to 20 µM, preferably 0.02 to 10 µM, while the concentration of CD4-PE40 is 0.1 to 100 nM, preferably 1 to 10 nM.

In another embodiment, the present invention provides reagents useful for carrying out the present process. Such reagents comprise a DNA fragment containing an HIV-protective gene, a coating solution and a small, inert, dense particle. The DNA fragment, coating solution, and the small, inert, dense particle are those described above.

Preferably, the DNA is frozen or lyophilized, the coating solution is frozen or maintained at 4° C., and the small, inert, dense particle is in a suspension in distilled water. Typically, the coating solution will contain saline. Alternatively, the dry ingredients for the coating solution may be premixed and premeasured and contained in a container such as a vial or sealed envelope.

The present invention also provides kits which are useful for carrying out the present method. The present kits comprise a first container means containing the above-described frozen or lyophilized DNA. The kit also comprises a second container means which contains the coating solution or the premixed, premeasured dry components of the coating solution. The kit also comprises a third container means which contains the small, inert, dense particles in suspension. These container means can be made of glass, plastic or foil and can be a vial, bottle, pouch, tube, bag etc. The kit may also contain written information, such as procedures for carrying out the present method or analytical information, such as the amount of reagent (e.g., moles or mass of DNA) contained in the first container means. The written information may be on any of the first, second, and/or third container means, and/or a separate sheet included, along with the first, second, and third container means, in a fourth container means. The fourth container means may be, e.g., a box or a bag, and may contain the first, second, and third container means.

The present invention will now be explained in further detail in the context of introducing Rev M10, a HIV-protective gene, into T cells. However, it is to be understood that similar results may be obtained using other foreign genes and other types of cells.

Replication of the human immunodeficiency virus (HIV) is controlled by complex interactions between its genome, virally encoded regulatory proteins and cellular factors (Vaishnav, Y. N., Wong-Staal, F., *Annu. Rev. Biochem.*, vol. 60, pp. 577–630 (1991)). Of these viral proteins, Tat and Rev play critical roles during the early stages of HIV replication. Tat is a 16 kDa protein derived from two exons (Goh, W. C., Rosen, C., Sodroski, J., Ho, D. D. & Haseltine, W. A., *J. Virol.*, vol. 59, pp. 181–184 (1986); Sodroski, J., Patarca, R., Rosen, C., Wong-Staal, F. & Haseltine, W., *Science*, vol. 229, pp. 74–77 (1985)) and primarily acts at the level of transcriptional elongation and/or initiation by interacting with the cis-acting Tat-responsive element (TAR) located in the RU5 region of the long terminal repeat (LTR) (Selby, M. J., Bain, E. S., Luciw, P. A. & Peterlin, B. M., *Genes Dev.*, vol. 3, pp. 547–558 (1989)). Tat is essential for viral replication as defective mutants make virus very inefficiently unless Tat is present (Fisher, A. G., Feinberg, M. B., Josephs, S. F. et al., *Nature*, vol. 320, pp. 367–371 (1986); Dayton, A. I., Sodroski, J. G., Rosen, C. A., Goh, W. C. & Haseltine, W. A., *Cell*, vol. 44, pp. 941–947 (1986)).

Whereas Tat dramatically augments RNA levels, Rev is a nuclear protein with a molecular weight of 19 kDa (Cullen, B. R., et al., *J. Virol.*, vol. 62, pp. 2498–2501 (1988)) which acts primarily post-transcriptionally to enhance the nuclear transport of unspliced message encoding structural proteins. This process requires interaction between Rev and a cis-acting RNA sequence designated the Rev-responsive element (RRE) located within the structural gene for the Env protein. The RRE consists of 234 nucleotides and can assume a highly complex secondary structure consisting of a putative central stem and five stem loop structures (Cochrane, A. W., Chen, C. H. & Rosen, C. A., *Proc. Natl. Acad. Sci. USA*, vol. 87, pp. 1198–1202 (1990); Heaphy, S., Dingwall, C., Ernberg, I. et al., *Cell*, vol. 60, pp. 685–693 (1990)). Mapping has shown that sequences within stem-loop 2 are the major binding sites for Rev. Mutations in Rev result in greatly decreased viral structural protein synthesis. Rev is thus essential for viral replication and infectious particle formation (Sodroski, J., Goh, W. C., Rosen, C., Dayton, A., Terwilliger, E. & Haseltine, W., *Nature*, vol. 321, pp. 412–417 (1986)). One mutant form of Rev, M10, has been previously shown to inhibit HIV replication in a dominant negative fashion (Malim, M. H., Bohnlein, S., Hauber, J. & Cullen, B. R., *Cell*, vol. 58, pp. 205–214 (1989)). This gene product confers resistance to HIV infection without affecting T-cell function (Malim, M. H., Freimuth, W. W., Liu, J. et al, *J. Exp. Med.*, vol. 176, pp. 1197–1201 (1992); Bevec, D., Dobrovnik, M., Hauber, J. & Bohnlein, E., *Proc. Natl. Acad. Sci. USA*, vol. 89, pp. 9870–9874 (1992); Bahner, I., Zhou, C., Yu, X- J., Hao, Q-L., Guatelli, J. C. & Kohn, D. B., *J. Virol.*, vol. 67, pp. 3199–3207 (1993)).

To adapt these molecular genetic strategies to clinically useful protocols for AIDS patients, an important step is to achieve the appropriate level of expression of the therapeutic gene in the relevant target cells. Preferably, the introduced gene is expressed and up-regulated as a consequence of an HIV infection itself, thereby giving optimal protection. Unfortunately, most of the present vector systems for gene therapy use constitutive expression vectors regulated by viral or cellular promoters. In the experiments described in the Examples section, results are presented for a vector which takes advantage of three features of HIV gene expression to achieve antiviral effects, including the ability to respond to Tat, serve as a TAR decoy and inhibit Rev function through the synthesis of Rev M10. The regulated expression achieved by this vector improves the protection against productive HIV replication in susceptible cells.

Several previous approaches have been attempted using RNA decoys for both Tat and Rev (Sullenger, B. A., Gallardo, H. F., Ungers, G. E., G. E. & Gilboa, E., *Cell*, vol. 63, pp. 601–608 (1990); Sullenger, B. A., Gallardo, H. F., Ungers, G. E. & Gilboa, E., *J. Virol.*, vol. 65, pp. 6811–6816 (1991)); however, these RNA structures could potentially interact with normal cellular factors and adversely affect normal cell function. A dominant mutant form of Rev, M10 (Malim, M. H., Bohnlein, S., Hauber, J. & Cullen, B. R., *Cell*, vol. 58, pp. 205–214 (1989)) inhibits the action of Rev without affecting T-cell function (Malim, M. H., Freimuth, W. W., Liu, J. et al, *J. Exp. Med.*, vol. 176, pp. 1197–1201 (1992)). Rev M10 can bind to RRE with a similar affinity as the wild type Rev protein and inhibits normal Rev function, presumably by competing for the binding sites required for normal Rev function (Malim, M. H., Bohnlein, S., Hauber, J. & Cullen, B. R., *Cell*, vol. 58, pp. 205–214 (1989)). Stable introduction and expression of the Rev M10 gene into CEM human T leukemia cells resulted in a marked reduction in HIV replication (Malim, M. H., Freimuth, W. W., Liu, J. et al, *J. Exp. Med.*, vol. 176, pp. 1197–1201 (1992)), indicating that the Rev M10 mutant represents a promising candidate for intracellular immunization in the control of HIV (Baltimore, D., *Nature*, vol. 335, pp. 395–396 (1988)). Other approaches have also been used to inhibit HIV replication, including other potential dominant negative mutant proteins (Trono, D., Feinberg, M. & Baltimore, D., *Cell*, vol. 59, pp. 113–120 (1989)), RNA decoys (Sullenger, B. A., Gallardo, H. F., Ungers, G. E., & Gilboa, E., *Cell*, vol. 63, pp. 601–608 (1990), catalytic RNA (Sarver, N., Cantin, E. M., Chang, P. S. et al., *Science*, vol. 247, pp. 1222–1225 (1990); Ojwang, J. O., Hampel, A., Looney, D. J., Wong-Staal, F. & Rappaport, J., *Proc. Natl. Acad. Sci. USA*, vol. 89, pp. 10802–10806 (1992); Yu, M., Ojwang, J., Yamada, O. et al., *Proc. Natl. Acad. Sci.*, USA, vol. 90, pp. 6340–6344 (1993)) and antisense oligonucleotides (Eck, S. L. & Nabel, G. J., *Curr. Op. Biotechnol.*, vol. 2, pp. 897–904 (1991); van der Krol, A. R., Mol, J. N. & Stuitje, A. R., *Biotechniques*, vol. 6, pp. 958–976 (1988); Izant, J. G. & Weintraub, H., *Science*, vol. 229, pp. 345–352 (1985)).

Figure 2:
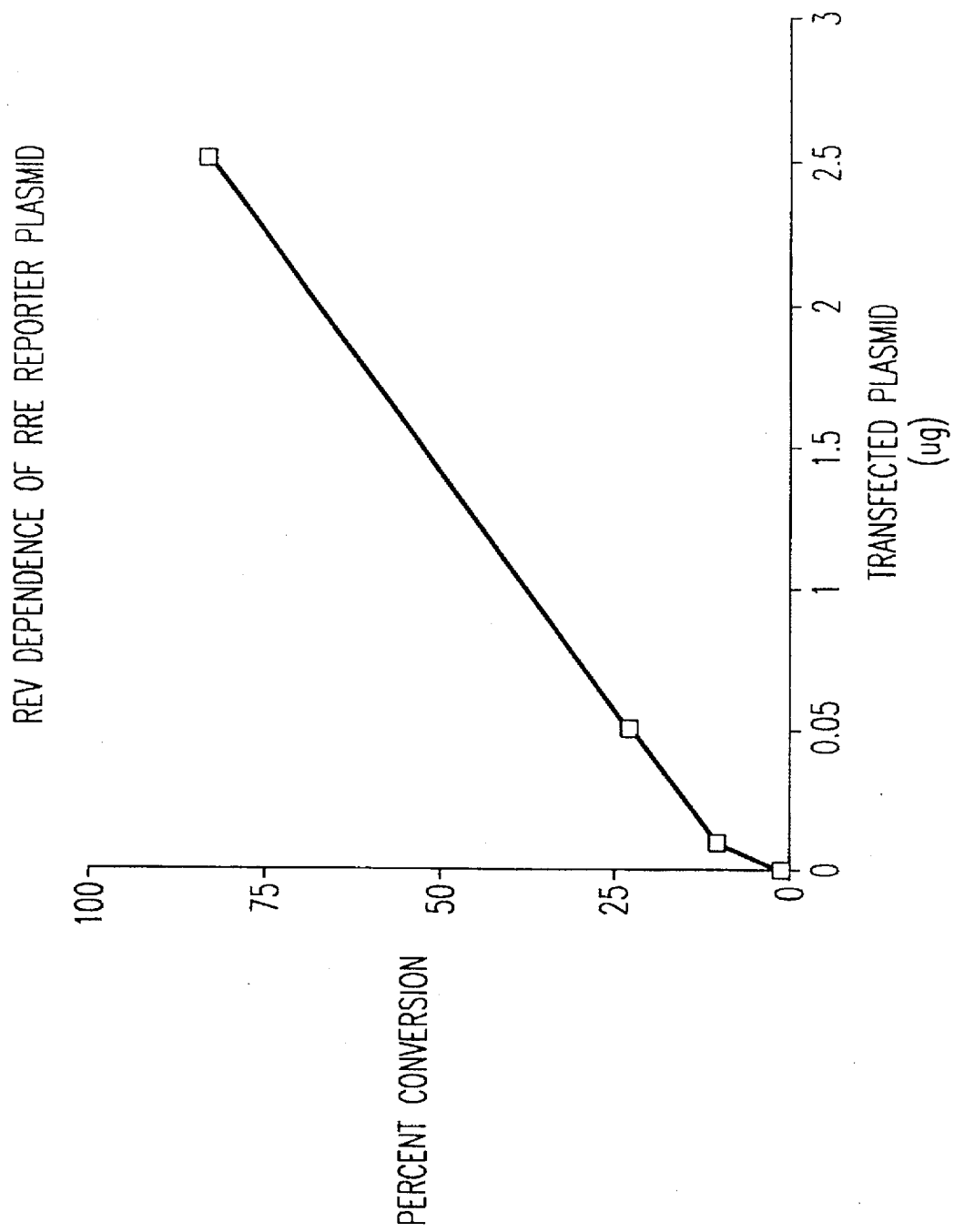
FIG. 2 illustrates the responsiveness of the RSV-CAT-RRE reporter to stimulation by Rev. The RSV-CAT-RRE reporter was transfected with the indicated amounts of RSV-Rev expression vector. Transfection and CAT assay procedures were performed as described in Materials and methods.
Figure 3:
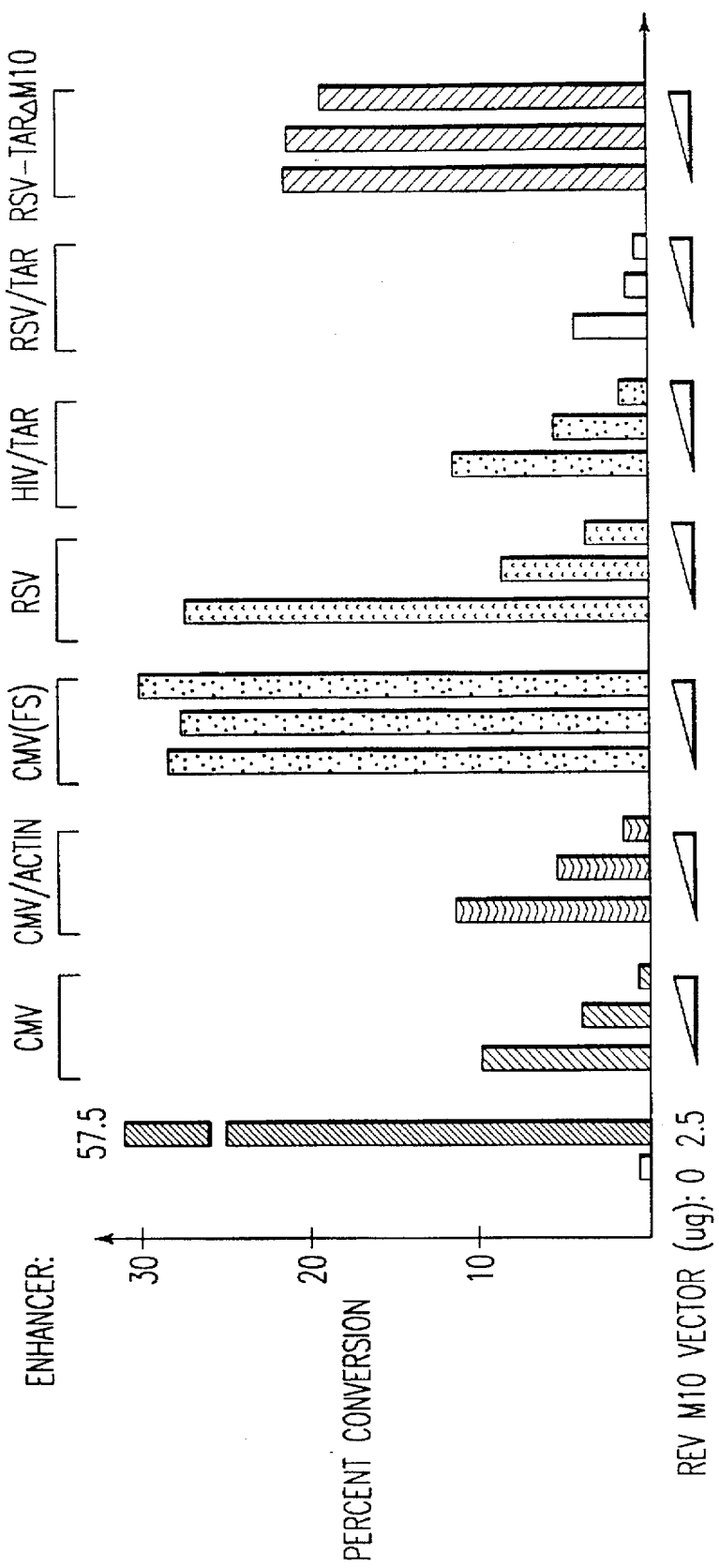
FIG. 3 provides a comparison of relative strengths of different enhancers. The Rev-responsive CAT reporter RSV-CAT-RRE (2.5 µg) and the RSV-Rev (2.5 µg) were cotransfected with 2.0, 5.0 and 10.0 µg of expression vectors driven by different promoters as shown. The relative effectiveness of each enhancer as determined by its ability to inhibit transactivation of RSV-CAT-RRE by the RSV-Rev expression vector is shown as a percentage of conversion of chloramphenicol to its acetylated forms in the presence of different M10 expression vectors. The first two bars represent RSV-CAT-RRE alone and RSV-CAT-RRE with 2.5 µg RSV-Rev.

The protective effects of the RSV/TAR Rev M10 vector are probably related to at least three effects on early viral gene expression. First, the increased level of basal transcription from the RSV/TAR promoter provides a higher level of Rev M10 to block the function of wild type Rev. A high basal level of expression appears to correlate with inhibition of virus replication and may result from the formation of mixed Rev/Rev M10 multimers, which may form more readily if Rev M10 is synthesized prior to wild type Rev in an infected cell. Second, Rev M10 expression is further induced by Tat produced from the early viral RNAs synthesized after HIV infection which binds to the TAR sequence of RSV TAR Rev M10 and produces more Rev M10 protein which inhibits Rev function. TAR, on the other hand, may contribute directly to the high-level of basal expression (FIG. 3). Finally, the synthesis of TAR RNA from the RSV promoter also provides a source of TAR RNA which can compete with the binding of Tat to the native promoter and also inhibits Tat function. At low Tat concentrations, the TAR decoy could limit Tat-mediated transactivation, although the TAR region would allow for further protection should this protective effect be overwhelmed. Thus, the combination of the RSV promoter with the TAR sequence appears to provide the best protection against HIV replication in vivo through this combination of autoregulatory elements. This expression vector provides significant antiviral effects and could potentially be used with other HIV protective proteins to provide protective effects in patients infected with HIV.

In the Examples described below, gold microparticles were used to achieve optimal transduction frequencies within T cells. Using this technique, ~10% of cells were routinely transduced. In general, the rates of transduction were ~10-fold higher than those achieved with retroviral vectors. Although expression was detected soon after gene transfer, cells could be maintained and selected for long periods of time (>2 months) in cell culture, indicating the stability of expression. This stability was confirmed by Southern blotting of cell lines which revealed a signal from integrated DNA, detectable as early as two weeks after transduction and selection in vivo.

The present method can be applied also to other relevant target cells, including hematopoietic stem cells and dendritic cells, which bind virus in the lymph node. It is possible to generate expression vectors for these HIV protective genes whose inhibition of viral spread can be optimized by appropriate regulation of gene expression (Liu, J., et al *Gene Ther.*, vol. 1, pp. 32–37 (1994)). The present method makes it possible to evaluate the efficacy of a variety of antiviral genes for the treatment of HIV infection in patients (Nabel, G. J., et al, *Hum. Gene Ther.*, vol. 5, pp. 79–92 (1994)). At the same time, the ability to introduce eukaryotic expression vectors into human primary peripheral blood lymphocytes by this method allows further analysis of the pathways of T cell activation responsible for the activation of specific transcription factors within these cells.

Other features of the invention will become apparent in the course of the following descriptions of exemplary embodiments which are given for illustration of the invention and are not intended to be limiting thereof.

EXAMPLES

I. Viral Transfection

Materials and Methods

Plasmids

The pRSV CAT-RRE plasmid was derived from a plasmid which utilized the SV40 enhancer, DM128 (Hope, T. J., Huang, X. J., McDonald, D. & Parslow, T. G., *Proc. Natl. Acad. Sci. USA*, vol. 87, pp. 7787–7791 (1990)). This plasmid was digested by BclI and HindIII to remove the SV40 promoter and then incubated with Klenow polymerase. The resulting backbone was ligated with a Klenow enzyme-treated NdeI-HindIII fragment containing the RSV promoter isolated from PSPRSV (Williams, T., Admon, A., Luscher, B. & Tjian, R., *Genes Dev.*, vol. 2, pp. 1557–1569 (1988)).

The RSV-Rev expression vector is a plasmid containing the Rev open reading frame (ORF) under the control of RSV promoter. The NcoI-XhoI fragment containing the complete ORF for Rev, from the CMV-Rev expression vector (Malim, M. H., Hauber, J., Le., S. Y., Maizel, J. V. & Cullen, B. R., *Nature*, vol. 338, pp. 254–257 (1989)) was ligated into the NcoI-XhoI sites of RSV p105 expression vector (Perkins, N. D., Schmid, R. M., Duckett, C. S., Leung, K., Rice, N. R. & Nabel, G. J., *Proc. Natl. Acad. Sci. USA*, vol. 89, pp. 1529–1533 (1992)) after removal of the original p105 insert with NcoI and XhoI. RSV or Rev M10 is similar to RSV-Rev, except that a NcoI-XhoI fragment containing the Rev M10 ORF from CMV-M10 was used.

The RSV-M10 expression vector used in the stable transfections was prepared from a parental RSV-ADH vector encoding the alcohol dehydrogenase (ADH) and neomycin resistance gene (Lin, W. -C. & Culp, L. A., *BioTech*, vol. 11, pp. 344–351 (1991)). A Klenow-treated NcoI-XhoI fragment containing the M10 ORF was ligated into Klenow-treated backbone after the ADH gene insert was removed by digestion with HindIII and XbaI.

The HIV Rev M10 expression vector contains the HIV LTR from –660 to +74 to enhance expression of the Rev M10 ORF. It was prepared from a NcoI-XhoI fragment containing the Rev M10 ORF from cRev (M10) treated with Klenow enzyme, ligated into the HindIII site of HIV-CAT (Nabel, G. & Baltimore, D., *Nature*, vol. 326, pp. 711–713 (1987) to generate HIV Rev M10/CAT. The HindIII site is regenerated in the ligation. HIV Rev M10/CAT was digested with XhoII and HindIII restriction enzymes. This XhoI/HindIII fragment containing the HIV LTR and Rev M10 ORF was treated with Klenow inserted into RSV-ADH vector (Lin, W. -C. & Culp, L. A., *BioTech*, vol. 11, pp. 344–351 (1991)) after the RSV promoter and ADH structural genes were removed with BglII and XbaI and treated with Klenow.

RSV/TAR Rev M10 contains the RSV promoter and sequence of TAR from –18 to –72 of HIV promoter to stimulate expression of the Rev M10 ORF. It was constructed by digesting HIV Rev M10/CAT described above with PvuII and HindIII. The 0.6 kb fragment containing the 80 base pair TAR sequence and Rev M10 ORF was isolated, treated with Klenow polymerase and ligated to the Klenow-treated HindIII and XbaI sites in the RSV-ADH vector (Lin, W. -C. & Culp, L. A., *BioTech*, vol. 11, pp. 344–351 (1991)) in which the ADH structural gene was excised. RSV/TAR ΔRev M10 is identical to RSV/Tar Rev M10 except that the initiation codon ATG was deleted by site-directed mutagenesis and the deletion confirmed by sequence analysis.

The HIV-CAT plasmid (Rosen, C. A., Sodroski, J. G. & Haseltine, W. A., *Cell*, vol. 41, pp. 813–823 (1985)) have been described previously.

Transfection and CAT assays

Transfection and CAT assays were performed as previously described (Nabel, G. & Baltimore, D., *Nature*, vol. 326, pp. 711–713 (1987)).

HIV infection

CEM cells (1×10$^6$) were inoculated with 2000 TCID$_{50}$ of HIV$^{Bru}$ for 2 hours at 37° C. (1:500 ratio HIV:CEM cells). The cells were then washed twice in fresh medium (RPMI-1640/10% fetal calf serum), resuspended at the original cell density and incubated at 30° C. Cultures were subcultured every 3 to 5 days depending on growth rate and duplicate samples taken for reverse transcriptase assays.

RT assays

Culture supernatants were assayed for RT activity as described previously (Potts, B. J., in *Techniques in HIV research*, Aldovini, A. and Walker, B. D. (eds.) Stockton Press: New York, pp. 103–106 (1990)). Poly(A)/oligo(dT) was used as template primer and incorporation of $^{32}$P-dTTP was measured after spotting 5 μl of the RT reaction mixture onto DE81 paper and washing with 2×sodium saline citrate (SSC) four times. Radioactivity was analyzed on a Betagene Betascope.

Results

Relative strength of different enhancers in Rev M10 expression vectors

Schematic diagrams of the regulatory elements utilized in these studies are illustrated (FIG. 1a). We prepared a reporter similar to others in which the 5' and 3' splice junctions of HIV are retained and the envelope gene is deleted, replaced by the chloramphenicol acetyl transferase (CAT) coding sequence with the Rev responsive sequence element (RRE) (Hope, T. J., Huang, X. J., McDonald, D. & Parslow, T. G., *Proc. Natl. Acad. Sci. USA*, vol. 87, pp. 7787–7791 (1990)). This reporter plasmid, RSV-CAT-RRE, utilizes Rous sarcomia virus (RSV), a strong constitutive regulatory element unresponsive to mitogen stimulation, and CAT activity is responsive to Rev, which presumably facilitates the transport of its mRNA from the nucleus to cytoplasm. Co-expression of Rev with this reporter increased CAT activity linear with Rev concentration (FIG. 1b). This reporter was used to analyze the activity of the dominant Rev M10 protein by measuring the level of inhibition of transactivation by the Rev expression vector (FIGS. 1 and 3).

To compare the effects of different promoters, we used alternative regulatory elements to stimulate expression of the Rev M10 gene. Regulatory regions included the RSV enhancer/promoter, a chimeric RSV/TAR promoter containing the RSV regulatory region linked to the 80 bp HIV-1 TAR sequence, and another TAR containing vector, the HIV LTR, was used to regulate Rev M10 expression. A frameshift mutant vector, RSV Tar FS, was used as a negative control. The HIV LTR represented a potentially attractive regulatory sequence for this purpose because it contains the native regulatory elements required for HIV transcriptional activation, but was less effective than RSV/TAR. The relative level of inhibition by Rev M10 expressed by these different regulatory sequence was assessed (FIG. 3). Although the plasmid reporter was not tested in the presence of Tat, the presence of the TAR sequence conferred greater protection than the RSV enhancer without TAR, suggesting that this sequence may exert Tat-independent protective effects, and that this enhancer might show even greater efficacy in the presence of Tat which might be synthesized after HIV infection.

Tat-stimulated expression of RSV/TAR Rev M10

Figure 4:
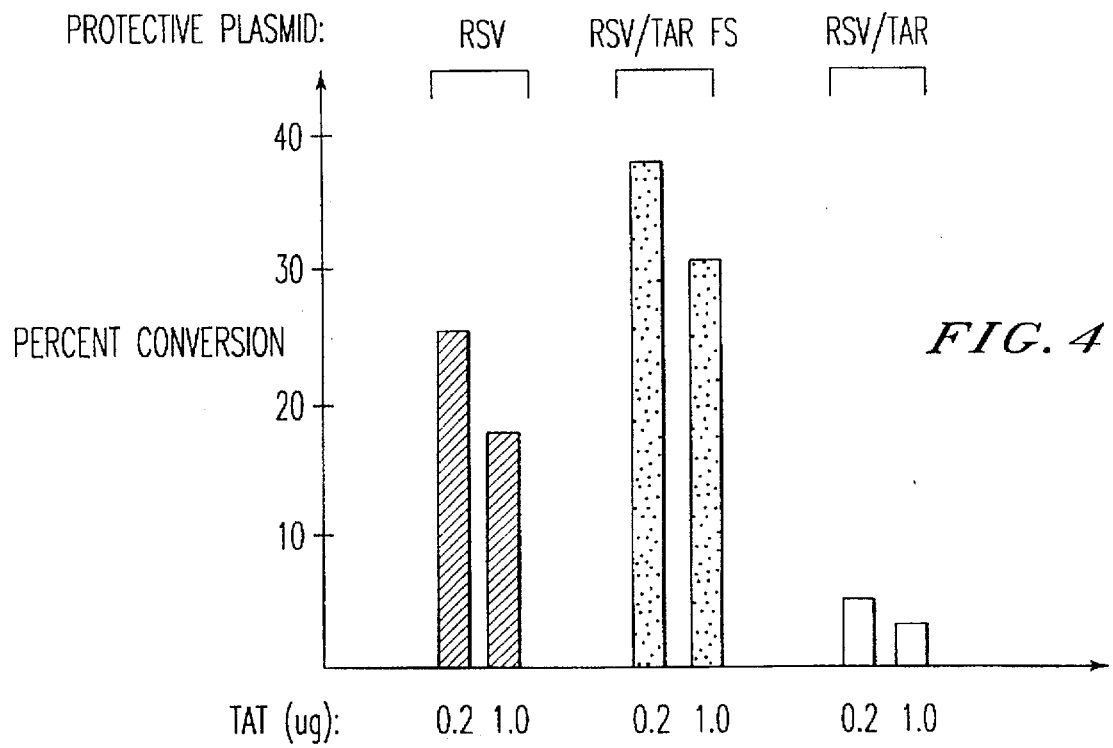
FIG. 4 shows the effect of Tat on RSV/TAR Rev M10 protection. The RSV-CAT-RRE reporter (2.5 µg) and RSV-Rev (2.5 µg) were cotransfected with RSV Rev M10 (2 µg), RSV-TAR Rev M10 (2 µg), or RSV TAR FS vectors (2 µg) and two different doses of pHD101 Tat expression vector (0.2 and 0.5 µg) or no (0.0) Tat expression vector (control). The activation of RSV-CAT-RRE by RSV-Rev is similar to that shown in FIG. 2. The inhibition of CAT conversion by the indicated vectors relative to the control is shown for each plasmid. Total transfected plasmid was normalized to 8 µg using Bluescript plasmid.

To determine whether RSV/TAR can function as an HIV-inducible regulatory region to stimulate the expression of Rev M10 gene following HIV infection (i.e., when Tat protein is synthesized), we compared the protective effects of the RSV and RSV/TAR vectors in the presence of a Tat expression plasmid. Each of these Rev M10 plasmids (2 μg) was cotransfected with a Tat expression plasmid to determine whether co-expression of Tat provides additional protection. RSV/TAR Rev M10 exerted a greater protective effect in the presence of the Tat expression plasmid. An identical plasmid lacking the TAR element showed minimal response to Tat (FIG. 4). The TAR sequence in combination with a strong constitutive enhancer, RSV, could therefore facilitate the expression of Rev M10 in the presence of Tat.

TAR decoy effect

Figure 5:
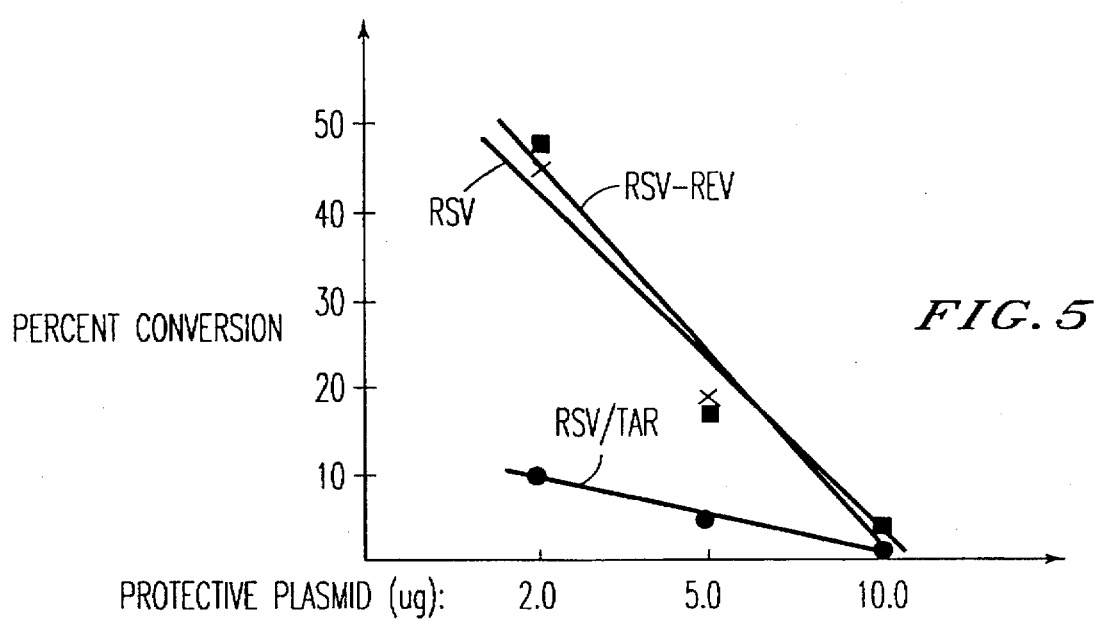
FIG. 5 shows the inhibition of Tat-mediated transactivation of HIV-CAT by RSV/TAR. HIV-CAT (1 µg) was cotransfected with pHD101Tat (0.2 µg) and 2.0 µg RSV expression vector without insert, RSV Rev M10, RSV Rev, or RSV/TAR Rev M10.

Because the RSV/TAR vector shows a high level of constitutive expression, it could also synthesize TAR RNA which could act as a decoy for Tat protein. Although TAR decoy effects have been previously described in specially designed retroviral vectors using a pol III promoter (Sullenger, B. A., Gallardo, H. F., Ungers, G. E., & Gilboa, E., *Cell*, vol. 63, pp. 601–608 (1990)), it was unknown whether this effect might be seen with a pol II promoter in a standard eukaryotic expression vector. In theory, TAR RNA could serve as a trans-acting competitor when the RSV/TAR Rev M10 vector is present in the cell by competing for binding to Tat protein required for transcription stimulated by the HIV LTR. To address this question, we used HIV-CAT, which contains the HIV LTR and TAR linked to the CAT gene, as the reporter plasmid. HIV-CAT was cotransfected with a constant amount of Tat expression vector in the presence of increasing amounts of the RSV promoter without an insert, RSV Rev M10, RSV Rev or RSV/TAR Rev M10. The Tat expression plasmid stimulated the expression from HIV-CAT 50-fold, and RSV/TAR Rev M10 reduced the level of transactivation by Tat$\approx$80%, compared to RSV Rev M10 or RSV without an insert (FIG. 5). As the only difference between RSV/TAR Rev M10 and RSV Rev M10 is the presence of the additional 80 base pair TAR sequence present in RSV/TAR-M10, these results suggest that the TAR region competes for Tat binding to the HIV-CAT reporter plasmid, and that it acts as a decoy in the context of the RSV/TAR vector.

Efficacy of different expression vectors for protection against HIV replication

Figure 6:
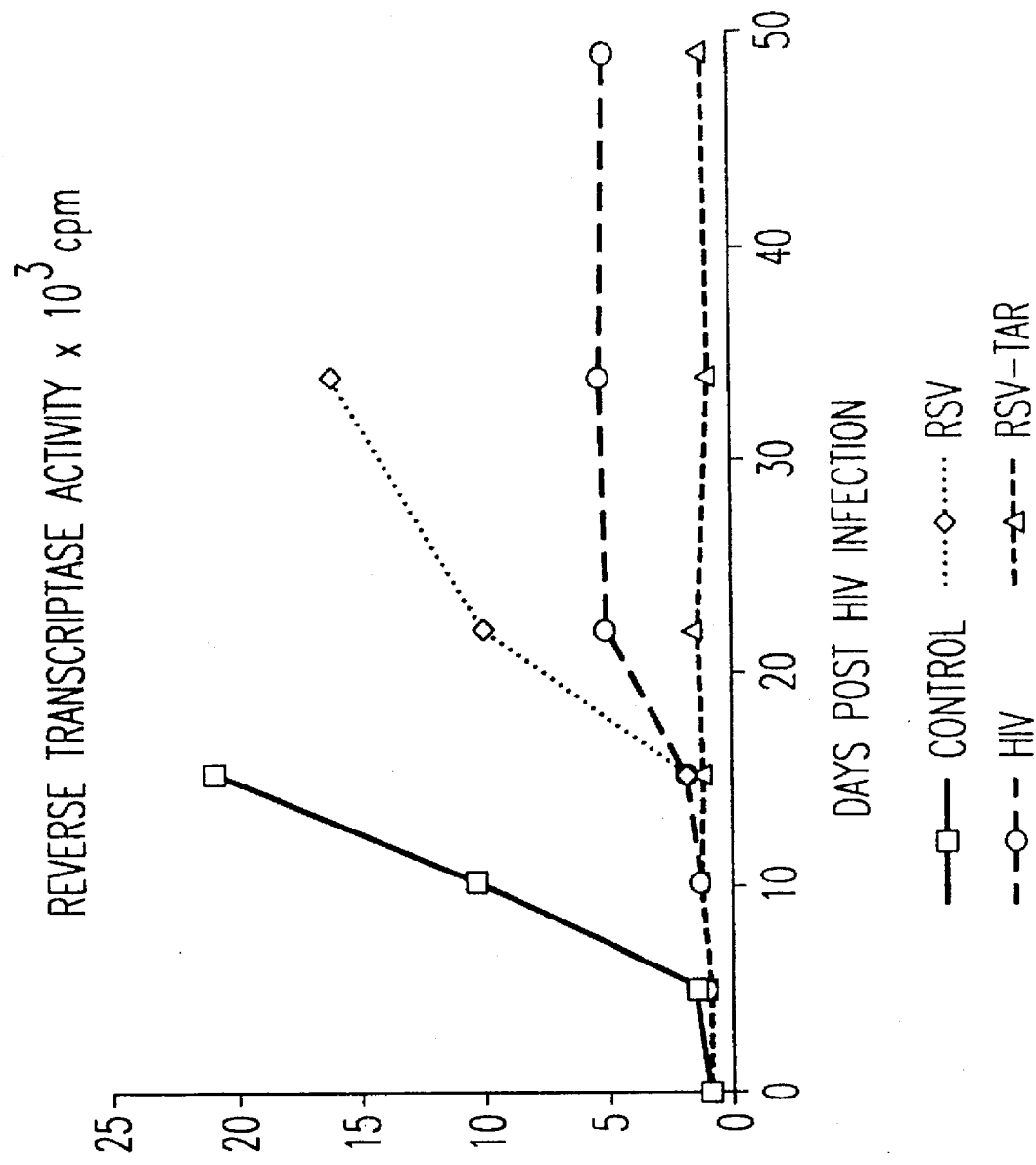
FIG. 6 shows the effects of expression regulated by RSV, HIV LTR, or RSV/TAR; control untransfected CEM cells or CEM cells stably expressing Rev M10 from the indicated promoters were incubated with HIV$^{Bru}$ (1:500 ratio TCID$_{50}$ HIV:CEM cells) for 2 hours, washed twice and resuspended in fresh medium. Culture supernatants were then assayed for RT activity at various times postinfection. Cultures were split every 3 to 5 days dependent on growth rate.
Figure 7A:
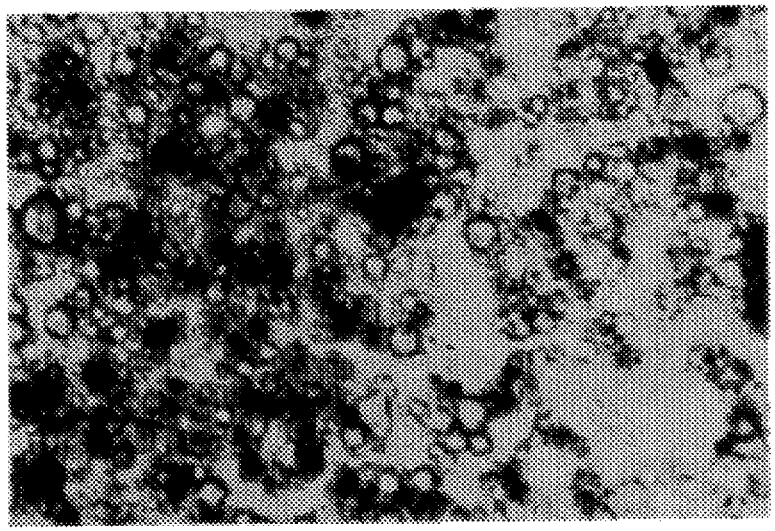
FIGS. 7a and 7b illustrate the protective effect of Rev M10 expressed in CEM cells after HIV infection. Control CEM cells (FIG. 7a) and CEM cells stably expressing Rev M10 (FIG. 7b) from the RSV/TAR construct were infected with HIV$^{Bru}$ as described in the Materials and Methods section below. Cells were then washed and monitored for cytopathic effects. The photographs are of cultures 5 days postinfection.
Figure 7B:
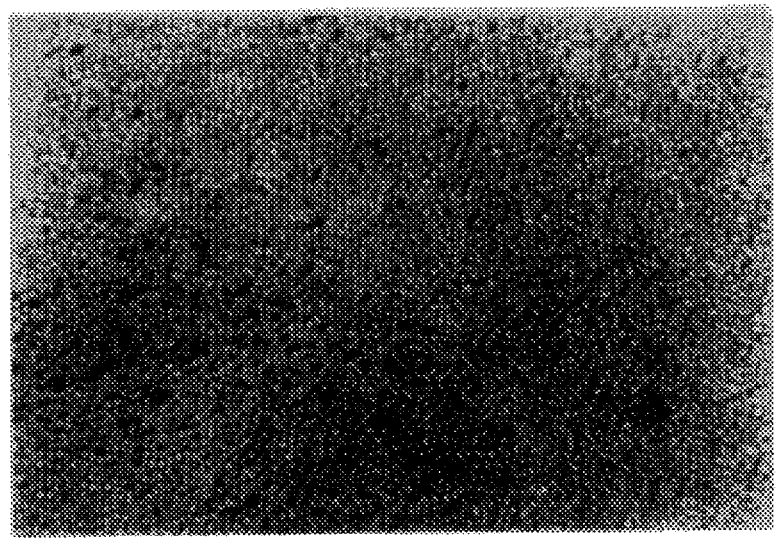

Three plasmids, RSV Rev M10, HIV Rev M10 and RSV/TAR Rev M10, were inserted into a plasmid which contains the G418 resistance gene (Lin, W. -C. & Culp, L. A., *BioTech*, vol. 11, pp. 344–351 (1991)) and transfected into CEM human T-cell leukemia cells. Stable pools of resistant cells were selected in the presence of G418. Cells stably expressing Rev M10 were subsequently challenged with HIV$^{Bru}$. The kinetics of cell survival from these lines containing different protective plasmids are shown in (FIG. 6). Control CEM cells began to show syncytia and cell death 5 days after HIV infection (FIG. 7). RSV Rev M10 provided protection for up to 15 days, whereupon the cells began to show cytopathic effects (CPE), although not at the same rate as control cells. HIV Rev M10 and RSV/TAR Rev M10 expressing cells showed protection from CPE up to 49 days, although the HIV Rev M10 cultures showed levels of reverse transcriptase (RT) above baseline indicative of a constant level of HIV RT production in the culture. The CEM cells transduced with HIV Rev M10 showed very few syncytia during the time-course, and RSV/TAR Rev M10 expressing cells showed no CPE throughout the entire 49 days of cell culture. Minimal RT activity was detected in these cultures but was above baseline levels, as previously noted (Malim, M. H., Freimuth, W. W., Liu, J. et al, *J. Exp. Med.*, vol. 176, pp. 1197–1201 (1992)). At lower multiplicities of infection (e.g., 1:500 ratio HIV:CEM) all the Rev M10 expressing cells survived infection for at least 4–5 weeks (i.e., the total course of the experiment), whereas the CEM control cells were not protected and showed extensive CPE within 2 weeks. In general, similar relative degrees of protection were seen with these different regulatory regions when cells were challenged with increasing amounts of virus (data not shown).

II. Particle-Mediated Gene Delivery System

Plasmid

The plasmid that was observed to be most effective with the particle-mediated gene delivery system contains the components listed below:

a.) Rev M10 or ΔRev M10 gene—This gene was described in the previous section.

b.) pSV2neo gene—This gene functions to confer neomycin resistance, as described above.

c.) RSV-tar—This consists of the RSV enhancer and TAR, a tat responsive element that is specific to the HIV system. This element proved to be most effective in experiments designed to test expression of Rev M10.

Particle-mediated gene delivery system

In this system, the vector that was described in the previous section is linearized with restriction enzymes and precipitated onto gold beads. The beads are resuspended in 100% ethanol and layered onto mylar sheets at a predetermined concentration. The target cells are then separated from the mylar sheets by a screen. Expansion of a helium gas causes a rupture disk to release at a fixed pressure, forcing the mylar sheet against the screen. The mesh allows the beads to pass through, while acting as a barrier to the mylar.

Particle-Mediated Gene Delivery Vectors

CD4$^+$ human T cells are isolated as described above. The cells are stimulated as described above with anti-CD3 for 24 hours before undergoing particle-mediated gene delivery with DNA coated gold beads. The beads are coated with linearized plasmid (previously digested with the Aat II), precipitated onto the gold beads, resuspended in 100% ethanol, and layered onto mylar sheets. The cells are stimulated with anti-CD3 and IL-2 or anti-CD3 and anti-CD28. Cells will be re-infused only if 0.1% of the cells are transduced successfully. No penicillin or other beta-lactam antibiotics are used in the culture of these cells.

Preparation of Human T-Cells

The patients T cells are obtained by leukapheresis, and they are transferred to sterile 75 cm$^2$ vented cap tissue culture flasks (Corning). 60 mls of AIM V media containing 5% human AB sera (50 U/ml IL 2) is added to each flask. The final cell density is 5×10$^5$/ml.

Selection of CD4$^+$ cells

CD4$^+$ cells are enriched by eliminating CD8$^+$ cells by selection with AIS CD8 CELLector culture flasks, following the manufacturers procedures.

Cells are cultured in a 37° C./5% CO$_2$ incubator as indicated below.

Stimulation of Cells

Cells are stimulated for 24 to 48 hours by either anti-CD3 plus IL2 (50 U/ml) or the simultaneous addition of anti-CD3 plus anti-CD28 (0.25 μg/ml) final concentration. Immediately prior to particle delivery, cells are concentrated by centrifugation and resuspended at 5×10$^6$ cells in 100 μl of AIM V medium, and transferred from the 75 cm$^2$ vented top tissue culture flask to 60 mm diameter petri dishes. The cells are spread out over a 4 cm$^2$ area in the center of the 60 mm dish using a small pipette tip. The cells are transduced at this concentration.

DNA Preparation

RevM10 containing vectors

The DNA's are linearized by cutting with AatII restriction enzyme. The DNA is then phenol/chloroform extracted and ethanol precipitated. DNA is resuspended at a concentration of 1 mg/ml in TE.

Microcarrier Preparation (120 treatments using 500 μg gold beads per delivery)

60 mg of gold 1.0 μm microparticles will be aliquoted in quantities of 3.0 mg per 1.5 ml microcentrifuge tube in each lot. One tube is used per treatment. The master lot is prepared as follows:

Add 1 ml of 70% ethanol freshly prepared.

Vortex for 3–5 minutes.

Incubate for 15 minutes.

Pellet the microparticles by spinning for 5 seconds in an Eppendorf microcentrifuge.

Remove the liquid and discard.

Repeat the following steps three times:

Add 1 ml of sterile water.

Vortex for 1 minutes at # setting.

Allow the particles to setter for 1 minute.

Pellet the microparticles by spinning for 2 seconds in a microcentrifuge.

Remove liquid and discard.

Add sterile 50% glycerol (Sigma, USP grade) to bring the microparticle concentration to 60 mg/ml (assume no loss during preparation).

Coating DNA onto microcarriers

Vortex microcarriers prepared in 50% glycerol (60 mg/ml) for 5 minutes to resuspend and disrupt agglomerated particles.

To 50 μl (3 mg) of microcarriers to a 1.5 ml microcentrifuge tube, add in order, vortexing vigorously: 5 μl spermidine (0.1M). (Sigma, USP)

Continue vortexing for 2–3 minutes.

Allow the microcarriers to settle for 1 minute.

Pellet the microcarriers by spinning for 2 seconds in a microcentrifuge.

Remove the liquid and discard.

Add 140 μl of 70% ethanol without disturbing the pellet.

Remove the liquid and discard.

Add 140 μl of 100% ethanol without disturbing the pellet.

Remove the liquid and discard.

Add 48 μl of 100% ethanol.

Gently resuspend the pellet by tapping the side of the tube several times and then by vortexing at low speed for 2–3 seconds.

Remove six 6 μl aliquots of microcarriers and transfer them to the center of a macrocarrier. 500 μg of microcarriers is removed each time and spread evenly over the central 1 cm$^2$ of the macrocarrier using the pipette tip. Desiccate immediately and let dry for 25 minutes.

Operation of Particle Delivery System

Sterilization of Apparatus

The entire interior of the chamber is sprayed with 70% ethanol and left for 20 minutes, at which time any residual ethanol is removed by wiping with sterile 4×4 gauzes.

Sterilization of Consumables

Microcarrier and rupture discs are sterilized by immersion in 70% ethanol for four hours followed by drying in a sterile bio-safety cabinet. Batches of 50 discs will be sterilized at one time and tested for the presence of bacteria and fungi and then qualified as in the Certificate of Analysis. Microcarrier and rupture disks will be packaged individually in sterile autoclave bags. Stopping screens will be sterilized by autoclaving for 30 minutes at 121° C. individually in sterile autoclave bags.

Figure 8:
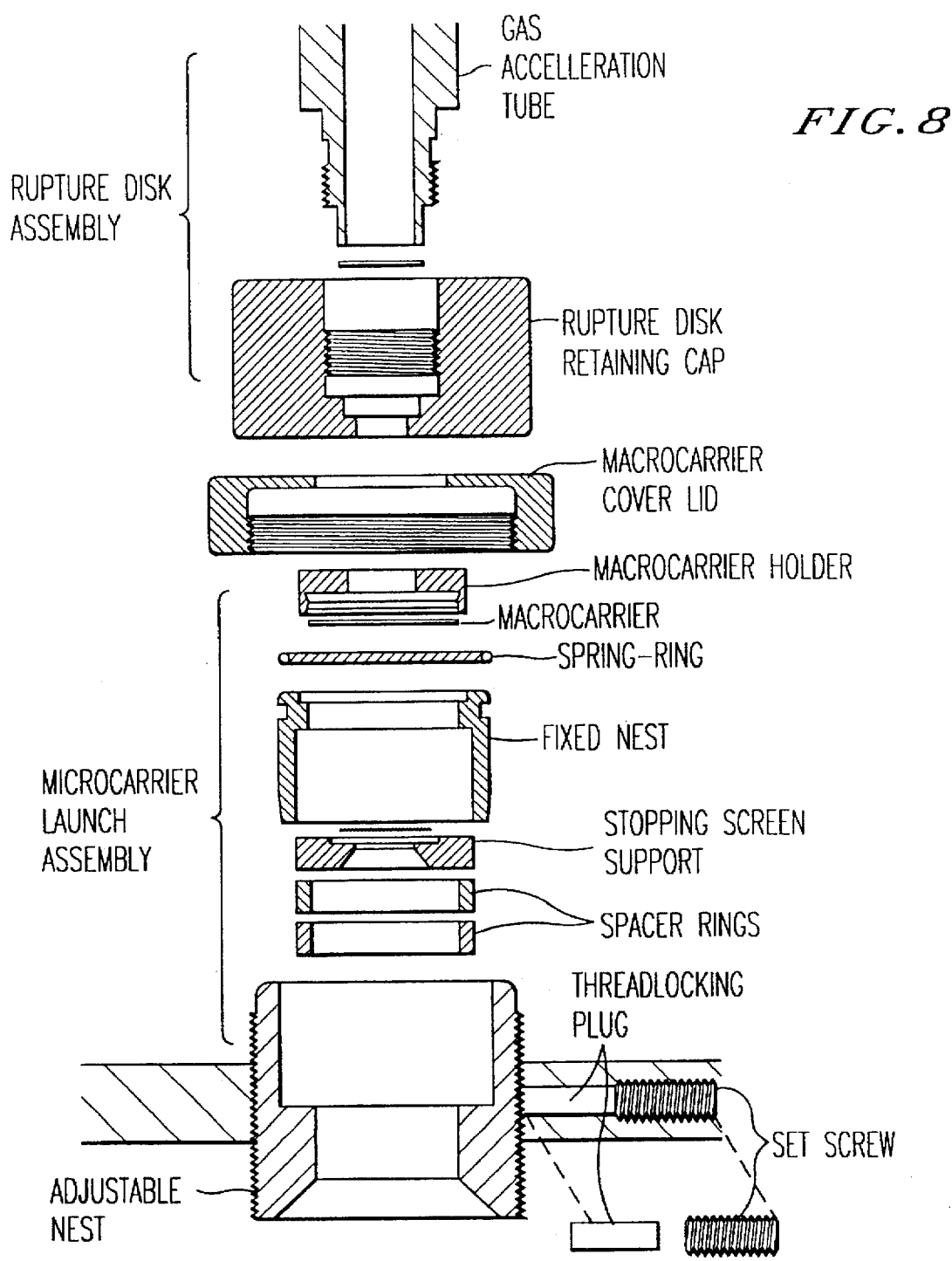
FIG. 8 is an expanded view of the rupture disk microcarrier launch apparatus.

Operational Directions See FIG. 8 for diagramatic view of the PDS.

Adjusting the Gap between Rupture Disk and Microcarrier

Mount the rupture disk retaining cap on the gas acceleration tube. Place the fixed nest containing the stopping screen support and spacer rings, and the macrocarrier holder in the adjustable next and secure the cover lid.

Release the set screw on the front of the microcarrier launch assembly with the smaller of the two hex key wrenches provided.

Turn the adjustable next until the distance between the rupture disk retaining cap and the macrocarrier cover lid is as desired. Three (3) gas adjustment tools (⅛", ¼" and ⅜") have been provided to reproducibly set the distance. A ¼" distance has been found to be optimal for the proposed studies.

Loading the Rupture Disk

Unscrew the rupture disk retaining cap from the gas acceleration tube. Do not remove the acceleration tube.

Place a rupture disk of the desired burst pressure in the recess of the rupture disk retaining cap.

Screw the rupture disk retaining cap onto the gas acceleration tube using a counter-clockwise motion as viewed from the top, and hand-tighten the cap.

Figure 9:
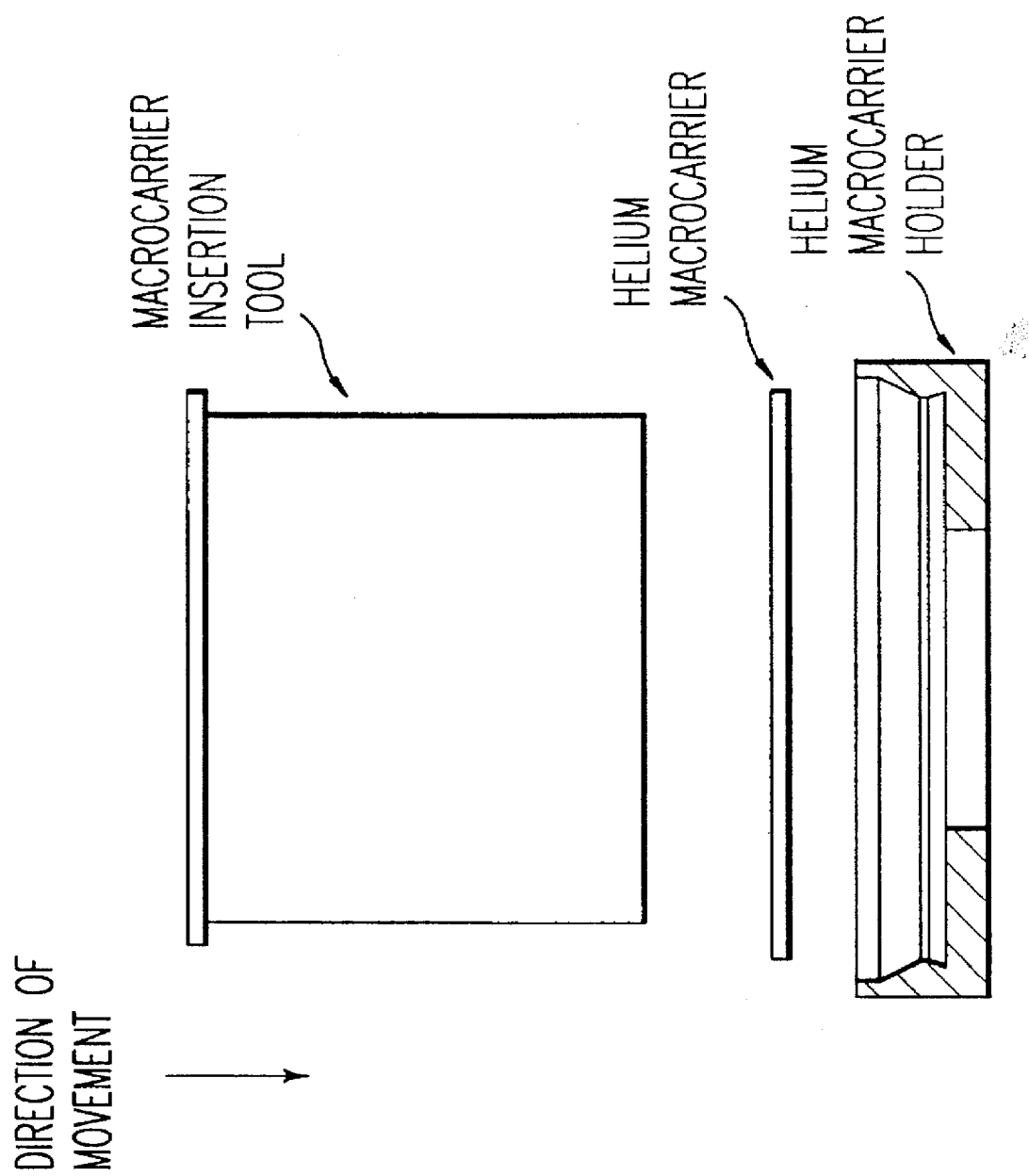
FIG. 9 illustrates the placement of the microcarrier in the microcarrier holder.
Figure 10:
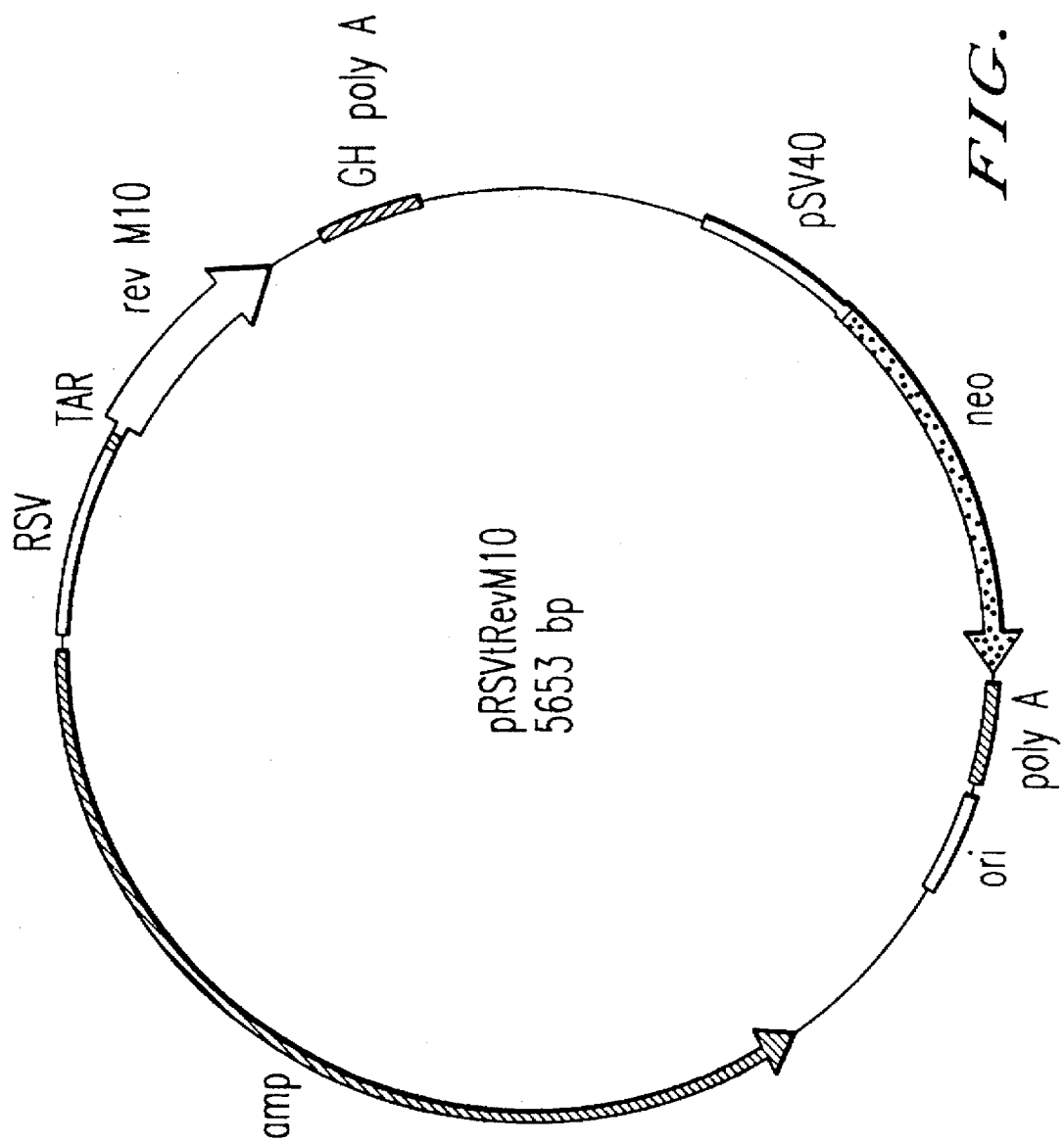
FIG. 10 is a schematic diagram of the plasmid pRS-VtRevM10.

Loading the Microcarrier Launch Assembly See FIG. 9.

Remove the microcarrier launch assembly from the sample chamber.

Unscrew the macrocarrier cover lid from the assembly.

Place a sterile stopping screen on the stopping screen support.

Install the macrocarrier holder with macrocarrier on the top rim of the fixed nest. The microcarrier should be facing down towards the stopping screen.

Place the macrocarrier cover lid on the assembly and turn clockwise until snug; it doesn't have to be tight.

Place the microcarrier launch assembly in the second slot from the top in the sample chamber.

Positioning the Sample

Put the Petri dish containing the lymphocytes in 100 μl of AIM V medium on the Petri dish holder. Remove the lid. Place the Petri dish holder at the desired level inside the sample chamber.

Close the latch and sample chamber door.

Activating the System

Turn power on.

Confirm that the helium tank pressure regulator is set to 200 psi over the selected rupture pressure (i.e. using 1,800 psi rupture discs set 2,000 psi).

Turn vacuum pump on. Set the vacuum switch to the VAC position to evacuate the sample chamber to the desired level exceeding 5 inches of mercury.

Once the desired vacuum level is reached, put the vacuum switch in the HOLD position.

Press and hold the FIRE switch to allow pressure to build in the acceleration tube. A metering valve has been installed on the solenoid valve assembly to control the rate of fill of the gas acceleration tube. It should take about 12–15 seconds to fill to burst pressure.

The rupture disk should burst within 10% of the indicated rupture pressure. Although the actual burst valves may be different from the indicated ones due to the accuracy of the pressure gauge, the variation in burst pressure form bombardment to bombardment is less than 5%.

Release FIRE switch immediately after disk ruptures.

Release the vacuum in the sample chamber by setting the VACUUM switch to the VENT position.

After vacuum is released, open sample chamber door.

Remove Petri dish containing the cells, replace the top on the dish and remove to adjacent tissue culture hood. Immediately add 3 mls of fresh medium mix the cells gently and transfer to a 75 cm$^2$ flask containing 15 ml of AIM V medium. Culture cells at 37° C. for 2 days to allow the cells to recover from the transduction procedures.

Remove the microcarrier launch assembly. Discard the macrocarrier and stopping screen from the microcarrier launch assembly.

Unscrew the rupture disk retaining cap from the gas acceleration tube. Remove the remains of the rupture disk. Repeat process for each firing, replace new discs.

If system is not to be continuously used, close main valve on the helium cylinder. Thoroughly clean sealing edges on the gas acceleration tube and rupture disk retaining cap.

Results 0.1–10% recombinant gene expression has been achieved in activated CD4+T lymphocytes, using this technique. In unstimulated cells, which may be used to transduce cells without concurrently inducing replication of virus in T cells which contain latent virus, 0.1% transduction efficiencies are observed. Experiments to test for the inhibition of HIV replication in cells in which Rev M10 was introduced using this method were performed. PCR analysis of HIV gag, and ELISA assays to detect p24 in the culture supernatants indicate that Rev M10 effectively inhibits productive replication of the virus, and proviral DNA. As noted previously, appropriate vectors to optimize expression of the gene in this system were developed. Plasmids that were constructed with different enhancers to determine which provided the most protection from HIV were evaluated. These tests were conducted by inserting each of the test enhancers, individually, into the Rev M10 vector and the control (ΔRev M10) vector, transfecting the vector into CEM cells, then infecting the cells with HIV. The RSV-TAR enhancer provided to be the most effective in these cells.

III. Comparison of Viral Transfection with Particle-Mediated Gene Transfer

Materials and Methods

Plasmids

RSV/TAR Rev M10 contains RSV promoter and sequence of TAR from −18 to −72 of HIV promoter to stimulate expression of the Rev M10 open reading frame (Liu, J., et al, *Gene Ther.*, vol. 1, pp. 32–37 (1994)). RSV/TAR ΔRev M10 is identical to RSV/TAR Rev M10 except that the initiation codon ATG was deleted and a linker inserted which was confirmed by sequence analysis. The HIV-CAT plasmid (Rosen, C. A., et al, *Cell*, vol. 41, pp. 813–823 (1985)) and the pHD101 tat plasmid (Markovitz, D. M., et al, *Proc. Natl. Acad. Sci. USA*, vol. 87, pp. 9098–9102 (1990)) have been described previously.

Isolation and passage of human peripheral blood lymphocytes

Blood for these studies was obtained from normal donors. Peripheral blood mononuclear cells were isolated using Ficoll-Hypaque separation. The cells were then stimulated in flasks coated with immobilized OKT3 monoclonal antibody and soluble IL-2 (50 U/ml) for 48–72 hours. Cells were recovered and resuspended at $5 \times 10^5$/ml in either AIM-V medium (BRL) or X-Vivo medium (MA Biowhittaker) containing 5% human AB serum+50 U/ml of IL-2. Cells were maintained at $5 \times 10^5 - 1.5 \times 10^6$/ml throughout the experiments.

Retroviral transduction

Freshly isolated human PBMC's from different donors were purified by centrifugation on Ficoll gradients as described previously. Cells were then stimulated by either treatment with 5 µg/ml PHA and 50 units/ml IL-2 for 48 hours or treatment with immobilized anti-CD3 and 50 units/ml IL-2 for up to 72 hours. Following stimulation, cells were infected for 6–12 hours with Ψ-Crip supernatants (plus 5 µg/ml polybrene) containing the PLJ-Rev M10 neo or frameshift PLJ-ΔRev M10 neo retroviruses (Malim, M. H., et al, *J. Exp. Med.*, vol. 176, pp. 1197–1201 (1992)). Cells were incubated at a density of $1 \times 10^6$ per well in a 24 well plate containing 1 ml of Crip supernatant and 1 ml of AIM-V medium. After infection, cells were washed once by centrifugation and resuspended at $5 \times 10^5$ cells/ml in conditioned AIM-V medium + 50 U/ml IL-2. Cells were then selected with 300 µg/ml G-418 (active).

Particle-mediated gene transfer

DNA was linearized by digestion with AatII restriction enzyme, extracted using phenol/chloroform, precipitated with ethanol, and resuspended in Tris-EDTA buffer (pH 8.0) to a final concentration of 1 mg/ml.

Gold microcarriers (60 mg, 1.6 µm microparticles) were washed with 1 ml of 70% ethanol, vortexed for 3–5 minutes, incubated for 2 minutes, and pelleted by microcentrifugation. The particles were then washed 3 times in sterile water (by adding water, vortexing for 1 minute, and allowing the particles to settle) and resuspended in 1 ml of 50% glycerol. 5 µg of the linearized DNA were added to 3 mg (50 µl) of the gold microcarriers. $CaCl_2$ (final concentration of 1M) and spermidine (final concentration of 16 mM) were added to the mixture. Graded ethanol washes were performed, and the pellet resuspended in 50 µl of 100% ethanol. 500 µg (8 µl) of the microcarriers were removed and spread evenly over the central 1 $cm^2$ of the mylar sheet. This was then desiccated and allowed to dry for 10–15 minutes before performing the bombardment procedure.

The apparatus was set up as described by the manufacturer (Biolistics PDS-1000/He System, Biorad Laboratories, Hercules, Calif.). The following adjustments were made. Rupture disk microcarrier gap ¾", microcarrier travel distance 6 mm, chamber vacuum 15 in Hg, Helium pressure 1800 psi and target distance 4 cm. Immediately prior to transduction, PBLs were centrifuged, resuspended to $5 \times 10^6$ cells/100 µl and the cell suspension spread over a 4 $cm^2$ area of a small petri dish (35×10 mm). After transduction, the cells are quickly removed from the petri dish and resuspended at $5 \times 10^5$ cells/ml in conditioned medium.

HIV infections

Cells were challenged with either $HIV^{BRU}$ or freshly passaged HIV clinical isolates $HIV^{CLIN}$. Cells ($1 \times 10^6$ cells/ml) were incubated with HIV at specific MOI for 2–4 hours at 37° C. Following the incubation, cells were washed with a 10× volume of fresh medium and resuspended at $5 \times 10^5$ cells/ml. Cells were maintained at a density of $0.5 \to 1.5 \times 10^6$ cells/ml throughout the infection.

Reverse Transcriptase assays

Culture supernatants were assayed for RT activity as described previously (Potts, B. J., *Techniques in HIV Research*, eds. Aldovini, A. & Walker, B. D. (Stockton Press, New York), pp. 103–106 (1990)). Poly A/oligo dT was used as the template primer and incorporation of $^{32}$P-dTTP was measured after spotting 5 µl of the RT reaction mixture onto DE81 paper and washing with 2× sodium saline citrate (SSC) four times. Radioactivity was analyzed on a Betagene Betascope.

Southern blotting

Genomic DNA from PBLs transduced with Rev M10 by particle-mediated gene transfer and selected for 2 weeks in G-418 (300 µg/ml) was isolated (Nabel, E. G., et al, *Hum. Gene. Ther.*, vol. 3, pp. 649–656 (1992)). DNA (5 µg) was resuspended in TE and digested with DraIII or DraIII/EcoRI for 4 hours at 37° C. The digested DNA was precipitated and electrophoresed on a 0.7% agarose gel. DNA was transferred to nitrocellulose and hybridized with a probe consisting of the entire Rev M10 gene labeled by oligonucleotide priming (Feinberg, A. P., et al, Anal. Biochem., vol. 132, pp. 6–13 (1983)). Conditions for hybridization and transfer were as described in (Nabel, E. G., et al, Hum. Gene. Ther., vol. 3, pp. 649–656 (1992)).

Results

Protective effects of Rev M10 in human PBL

To determine whether expression of Rev M10 could provide resistance to HIV infection in human lymphocytes, cells were transduced with a murine amphotropic retroviral vector pLJ Rev M10 (Malim, M. H., et al, J. Exp. Med., vol. 176, pp. 1197–1201 (1992)) or a frame-shifted Rev M10 negative control (pLJ ΔRev M10). Stimulated lymphocyte populations were transduced by retroviral infection with supernatants derived from Ψ-Crip amphotropic retroviral producer cells (0.5–5.0×10$^6$ G-418 resistant colonies/ml). After transduction, cells were selected in G-418 for 5–7 days prior to challenge with HIV. Retroviral transduction frequencies for the lymphocyte population 3 days post-transduction in anti-CD3/IL-2 stimulated PBLs were estimated by limiting dilution PCR analysis. Seven days after selection with G-418, the percentage of Rev transduced cells in the populations had increased to greater than 10%.

Figure 12A:
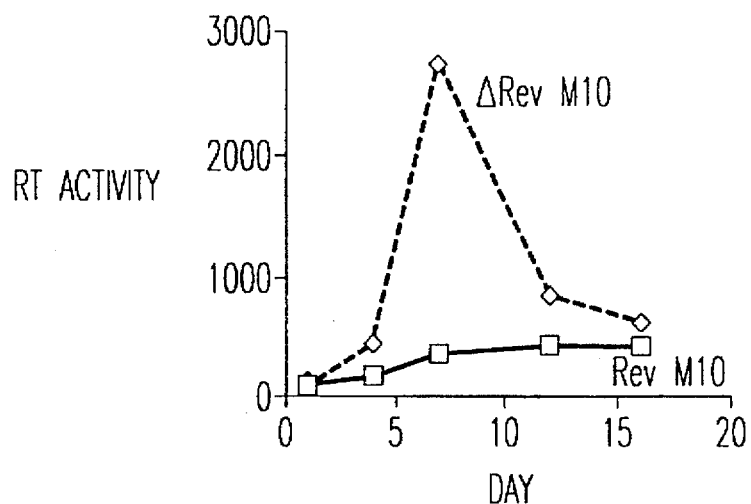
FIGS. 12a and 12b show the results of the challenge of Rev M10/ΔRev M10 retrovirally transduced human PBLs with HIV$^{BRU}$. PBLs were stimulated, transduced, and selected in G-418 for 1 week (see Examples). Cells were challenged with HIV at a MOI between 0.02 and 0.05.
Figure 12B:
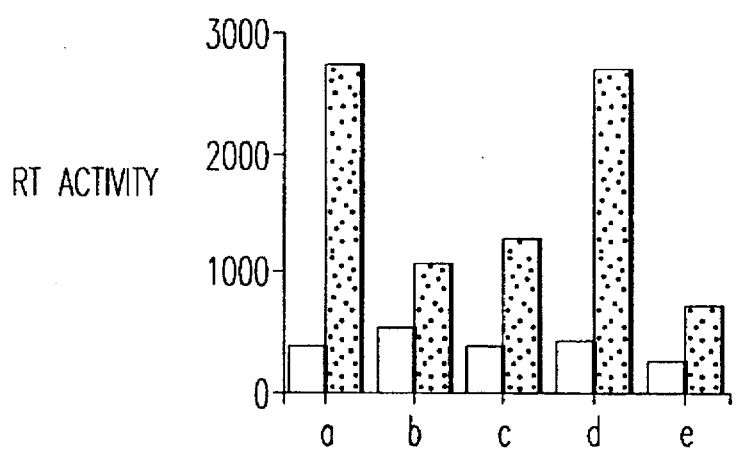

Following retroviral transduction and G-418 selection, cells were challenged with a cloned laboratory isolate, HIV$^{BRU}$. A time course following HIV challenge revealed a reduction in RT levels in Rev M10-transduced cells compared to ΔRev M10 negative controls. In addition, five independent experiments using lymphocytes from different HIV seronegative donors revealed a consistent reduction in culture supernatant HIV RT levels in Rev M10 retrovirally transduced compared to the frameshift control, ΔRev M10, cultures (FIG. 12b). It is important to note that viral replication was suppressed in both cases but was not completely abrogated, presumably because a significant proportion of cells did not contain the Rev M10 gene. These findings suggested that Rev M10 expression confers a significant level of protection from challenge with a cloned isolate of HIV. A nonspecific inhibitory effect was also seen when cells are grown in the presence of G-418, possibly because of its cytotoxic effect or through an effect on Rev (Zapp, M. L., et al, Cell, vol. 74, pp. 969–978 (1993)). This effect was also seen in HIV infection of untransduced lymphocytes, in which RT levels during infection ranged 2- to 3-fold higher than cells selected in G-418 (FIG. 12a).

To assess the potential for Rev M10 to affect viral replication in patients, human peripheral blood lymphocytes were challenged with freshly isolated clinical strains. Protection was observed when cells were exposed to these viruses. A representative time course of HIV infection showed a reduction in RT levels in Rev M10 cultures compared to ΔRev M10 over the 14-day course of the experiment (FIG. 13a). In addition, supernatant RT levels at the peak of HIV infection were consistently reduced in multiple independent Rev M10 transduced cells with at least two independent fresh isolated clinical strains (FIG. 13b).

Particle-mediated gene transfer into PBL: transduction frequencies and integration status To explore the potential efficacy of a nonviral vector delivery system, particle-mediated gene transfer was used to introduce expression plasmids into human PBL. Plasmids encoding Rev M10 or the frameshift mutant, ΔRev M10, under control of the RSV promoter and the HIV tat responsive element (Tar) (Liu, J., et al, Gene Ther., vol. 1, pp. 32–37 (1994)) were linearized by restriction enzyme digestion, precipitated onto gold microparticles and used to transduce PBLs by particle-mediated gene transfer. The frequency of gene transfer was determined by limiting dilution PCR. The percentage of cells initially transduced by this method was estimated to be at least 3% at 5 days post-transduction and increased to ≧50% by 21 days of selection in G-418 (Table 1). Cells could be maintained in the presence of G-418 for ≧2 months, suggesting that the transduced gene could be stably incorporated in the genome of these cells. To confirm this hypothesis, Southern blot analysis was performed. As early as 8 days post gene transfer, a signal corresponding to an integrated, but not a linear, form of the plasmid was detected (FIG. 16).

TABLE 1

Transduction frequencies of particle-mediated gene transfer into PBLs.

|   | Day | % Transduction |
|---|---|---|
| A. | 5–8 | 3–20 |
|   | 14–16 | >20 |
|   | 21 | >50 |
| B. | 5 | ≧10 |
|   | 12 | ≧15 |
|   | 22 | ≧25 |

Transduction frequencies for cells transduced by particle-mediated gene transfer were calculated by limiting cell dilution PCR analysis using Rev specific primers in (A) normal PBLs or (B) PBLs obtained from asymptomatic HIV positive donor and transduced in the presence of zelavirine and CD4-PE40. PBLs were transduced with Rev M10 expression plasmids as described in the Examples.

Resistance of cells transduced with a nonviral vector to HIV infection

Resistance of cells transduced with nonviral vectors was assessed after challenge with HIV$^{BRU}$ or fresh clinical isolates. A time course following HIV$^{BRU}$ challenge following transduction and G-418 selection revealed a reduction in RT levels in Rev M10-transduced cells compared to ΔRev M10 negative controls (FIG. 14a) similar to retrovirally transduced cells. Five independent experiments using lymphocytes from different HIV seronegative donors also revealed a consistent reduction in culture supernatant HIV RT levels in Rev M10 compared to the frameshift control, ΔRev M10, cultures (FIG. 14b). As with retroviral vectors, replication was suppressed but was not completely abrogated, because a significant proportion of cells did not contain the Rev M10 gene.

To assess the potential for Rev M10 to affect viral replication in fresh clinical isolates, human peripheral blood lymphocytes were challenged. Protection was observed when cells were exposed to these viruses over the 14-day course of the experiments (FIG. 15a). In addition, supernatant RT levels at the peak of HIV infection were consistently reduced in multiple independent Rev M10 transduced cells with at least two independent fresh isolated clinical strains (FIG. 15b).

Specific inhibition of endogenous HIV activation with HIV-1 antiviral agents

The process of T cell stimulation, needed to promote optimal gene transfer, also induces viral replication (Zagury, D., et al, Science, vol. 231, pp. 850–853 (1986)). In order to transduce and expand human PBLs derived from HIV-positive patients, activation of endogenous provirus must thus be avoided. To address this problem, conditions for activation and expansion of lymphocytes which selectively blocks productive HIV replication without affecting transduction efficiencies have been developed. This strategy employs a non-nucleoside reverse transcriptase inhibitor which specifically inhibits HIV-1 in vitro but does not affect murine retroviral reverse transcription. Two different agents were used including zelaviridine and nevirapine. Both inhibitors noncompetitively bind directly to HIV-1 reverse transcriptase (Richman, D., et al, *Proc. Natl. Acad. Sci. USA*, vol. 88, pp. 11241–11245 (1991); and Romero, D. L., et al, *Proc. Natl. Acad. Sci. USA*, vol. 88, pp. 8806–8810 (1991)). They were used alone or in combination with a second antiviral agent which exerts its effect on cells already infected with HIV. The second agent was a chimeric toxin protein consisting of a CD4 domain fused to Pseudomonas aeruginosa exotoxin A (CD4-PE40) (Chaudhary, V. K., et al, *Nature*, vol. 335, pp. 369–372 (1988)).

To determine whether a non-nucleoside RT inhibitor and CD4-PE40 could inhibit HIV replication in vitro and not interfere with transduction by the vector delivery system, the human renal epithelial cell, 293, was infected with a murine amphotropic retroviral vector encoding β-galactosidase (BAG) in the presence of these agents alone or in combination (Table 1). Either zelaviridine and nevirapine, alone or in combination with CD4-PE40, caused minimal inhibition of murine retroviral β-galactosidase transduction. At these concentrations, zelaviridine or nevirapine, alone or in combination with CD4-PE40, also effectively suppressed HIV replication to undetectable RT levels in freshly infected lymphocyte cultures over a 3-week period. In contrast, inhibition by azidothymidine (AZT), which is not HIV-1 selective, inhibited transduction by the murine retroviral vector (Table 2).

To evaluate the efficacy of these drugs in patient cells in vitro, lymphocytes from an asymptomatic HIV patient (CD4+ count ~400) were activated in their presence. Proviral HIV DNA content was determined by limiting dilution PCR 1 to 8 days after stimulation. A significant reduction in lymphocyte proviral DNA content was observed in antiviral treated cultures compared to untreated cells. Before treatment, between 1:250–1:2500 cells were HIV positive using gag specific primers. After treatment, ~1:25,000 were positive with nevirapine/CD4-PE40 and fewer than 1:50,000 with zelaviridine/CD4-PE40 treatment (the limit of the PCR detection system). No p24 antigen or reverse transcriptase activity was detected in culture supernatants. Thus, these agents were effective in reducing HIV activation in cell culture without interfering with the murine retroviral vector. Similarly, these agents had no effect on transduction efficiencies by particle-mediated gene transfer (Table 2).

TABLE 2

Effect of zelavirine, nevirapine, and CD4-PE40 on murine amphotropic retrovirus integration and expression.

| Treatment | Concentration | Positive Cells (%) |
|---|---|---|
| None | — | 85/82/93 |
| Zelaviridine | 1 µM | 70/95 |
| Zelaviridine | 5 µM | 73/81 |
| Zelaviridine | 20 µM | 26/45 |
| Nevirapine | 40 nM | 68/74 |
| Nevirapine | 100 nM | 97/83 |
| Nevirapine | 200 nM | 87/81 |

TABLE 2-continued

Effect of zelavirine, nevirapine, and CD4-PE40 on murine amphotropic retrovirus integration and expression.

| Treatment | Concentration | Positive Cells (%) |
|---|---|---|
| AZT | 2 µM | 0/1 |
| AZT | 10 µM | 0/0 |
| Nevirapine/CD4-PE40 | 40 nM/4 nM | 74/94 |
| Zelaviridine/CD4-PE40 | 1 µM/4 nM | 65/82 |
| Zelaviridine/CD4-PE40 | 5 µM/12 nM | 103/89 |

Murine amphotropic retroviral pLJ-β-gal supernatant (100 µl) produced from Ψ-Crip producer cells were inoculated onto 293 cells growing in 6 well plates. The wells contained 2 mls of medium with the indicated concentrations of antiviral compounds. After 3 days of incubation, cells were fixed and stained for β-gal activity by X-gal staining and the number of positive cells per duplicate well counted. Control untransduced cells showed no X-gal staining.

IV. Toxicity Studies on Particle-Mediated Gene Transfer System

Toxicity of DNA-coated Gold Particles

A safety consideration that is unique to particle-mediated gene delivery is the potential for injection of gold particles into patients. Although this possibility is unlikely, since the particles are removed by low-speed centrifugation prior to reinfusion of transduced cells, to address this question, DNA-coated gold particles were tested in mice to determine their potential for toxicity. Gold particles coated with RSV/Rev M10 plasmid were injected intravenously (8 mice) and a negative control group received normal saline (8 mice). The test group was injected with 0.8 µg DNA and 500 µg of gold microspheres (1000× greater than are likely to be inadvertently administered to patients). After ten days, the recipients were sacrificed, and the organs were removed and examined both grossly and histologically. Serum samples were obtained prior to injection and at the time recipient animals were sacrificed, and were analyzed for evidence of alterations is selected serum enzymes and chemistries. These studies demonstrated no signs of toxicity (see Tables 3 and 4 below).

TABLE 3

Intravenous Injection of RSV/Rev M10 Plasmid-Coated Gold Beads

| | PCR Analysis | | | | | | | |
|---|---|---|---|---|---|---|---|---|
| Mice | Brain | Heart | Kidney | Liver | Lung | Muscle | Ovary | Spleen |
| 1 | + | − | + | + | − | − | + | − |
| 2 | + | + | + | + | + | + | + | + |
| 3 | + | + | + | + | − | − | − | − |
| 4 | + | − | − | − | − | − | − | − |
| 5 | − | − | − | − | − | − | − | − |
| 6 | − | − | − | − | − | − | − | − |
| 7 | − | − | − | − | + | − | − | − |
| 8 | − | − | − | − | + | − | − | − |
| Total | 4/8 | 2/8 | 3/8 | 3/8 | 2/8 | 1/8 | 2/8 | 1/8 |

*Note - PCR Analysis was performed on the 8 mice that were injected with the RSV/Rev M10 plasmid-coated gold beads

TABLE 4

Intravenous Injection of RSV/Rev M10 Plasmid-Coated Gold Beads

| | | | | Organ Pathology | | | | |
|---|---|---|---|---|---|---|---|---|
| Mice | Brain | Heart | Kidney | Liver | Lung | Muscle | Ovary | Spleen |
| 1* | Normal | Normal[2] | Normal | Normal[1] | Normal | Normal | Normal | Normal |
| 2* | Normal | Normal | Normal | Normal | Normal | Normal | No data | Normal |
| 3* | Normal | Normal | Normal | Normal | Normal | Normal | Normal | Normal |
| 4* | Normal | Normal[2] | Normal | Normal | Normal | Normal | Normal | Normal |
| 5* | Normal | No data | Normal | Normal | Normal | Normal | Normal | Normal |
| 6** | Normal | Normal | Normal | Normal | Normal[3] | Normal | Normal | Normal |
| 7** | Normal | Normal | Normal | Normal | Normal[3] | Normal | Normal | Normal |
| 8** | Normal | Normal | Normal | Normal | Normal[3] | Normal | No data | Normal |
| 9** | Normal | Normal | Normal | Normal | Normal | Normal | Normal | Normal |
| 10** | Normal | Normal | Normal[4] | Normal[1] | Normal | Normal | Normal | Normal |
| 11* | Normal | Normal | Normal | Normal | Normal[3] | Normal | Normal | Normal |
| 12* | Normal | Normal | Normal | Normal | Normal[3] | Normal | Normal | Normal |
| 13* | Normal | Normal | Normal | Normal[1] | Normal[3] | Normal | Normal | Normal |
| 14** | Normal | Normal | Normal | Normal | Normal[3] | Normal | Normal | Normal |
| 15** | Normal | Normal | Normal | Normal | Normal[3] | Normal | Normal | Normal |
| 16** | Normal | Normal | Normal | Normal | Normal[5] | Normal | Normal | Normal |

*Mice injected with saline only
**Mice injected with RSV/Rev M10 plasmid-coated gold beads
The following are incidental findings of no pathological significance.
[1]Focal cluster of mononuclear inflammatory cells.
[2]Focal calcification of epicardium.
[3]Focal peribronchial lymphoid aggregates.
[4]Minimal focal very recent tubular necrosis.
[5]Focal endobronchial cluster of foamy macrophages. Focal peribronchial lymphoid aggregates. Focal interstitial macrophage clusters with particulate inclusions.

Additionally, studies have been performed with human CD4+ cells transduced with RSV/TARREV M10 by particle-mediated gene transfer. In three mice, $2\times10^7$ cells were injected intravenously per animal. No transformation or toxicity has been observed in one animal at one week, one animal at two weeks, or one animal at three weeks. Pathologic analysis of these animals was normal (Table 5).

TABLE 5

Intravenous Injection of CD4+ cells Transduced with the RSV/TAR Rev M10 Vector

| | | | Organ Pathology | | | | | |
|---|---|---|---|---|---|---|---|---|
| Mice | Vector | Time of Sacrifice | Heart | Kidney | Liver | Lung | Ovary | Spleen |
| Control | | 3 weeks | Normal | Normal | Normal | Normal | No data | Normal* |
| 1 | RSV TAR Rev M10 | 1 week | Normal | Normal | Normal | Normal | Normal | Normal* |
| 2 | RSV TAR Rev M10 | 2 weeks | Normal | Normal | Normal | Normal | No data | Normal* |
| 3 | RSV TAR Rev M10 | 3 weeks | Normal | Normal | Normal | Normal | No data | No data |

*All of the specimens of spleen had an absence of T cell regions, due to the immunodeficient nature of the mice Another mouse has been observed at two months without ill effects after receiving $4\times10^7$ transduced cells intravenously.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. A method for prolonging T cell survival in a HIV infected patient, comprising:
    (i) removing a plurality oft cells from a said patient;
    (ii) introducing, by particle mediated gene transfer, a gene encoding a product which inhibits HIV replication into said plurality of T cells; and
    (iii) reintroducing said plurality of T cells into said patient,
    wherein said gene encoding a product which inhibits HIV replication is Rev M10.

2. The method of claim 1, wherein said gene is under the operational control of a sequence of DNA such that the expression of said gene is stimulated by the expression of HIV.

3. The method of claim 1, wherein said gene is contained in a plasmid and is downstream from the TAR sequence such that expression of the gene is activated by Tat.

4. The method of claim 3, wherein said plasmid is pRSVtRevM10.

5. The method of claim 1, wherein said introducing by particle mediated gene transfer is carried out by introducing particles on which said gene is coated into said plurality of T cells, wherein said particles are made of a material selected from the group consisting of inert metals and inert plastics.

6. The method of claim 5, wherein said particles are made of a material selected from the group consisting of gold, silver, platinum, tungsten, polystyrene, polypropylene, and polycarbonate.

7. The method of claim 5, wherein said particles are gold particles.

8. The method of claim 5, wherein said particles have a diameter of 0.5 to 5 microns.

9. The method of claim 5, wherein said particles have a diameter of 1 to 3 microns.

10. The method of claim 5, wherein said gene is contained in a plasmid and said particles are gold particles, and said plasmid is coated on said particles in an amount of 3 to 30 micrograms of plasmid per milligram of particles.

11. The method of claim 10, wherein said particles are coated with an encapsulating agent before being coated with said plasmid.

12. The method of claim 11, wherein said encapsulating agent is polylysine.

13. The method of claim 1, wherein said gene is introduced into $10^9$ to $10^{13}$ T cells.

14. The method of claim 1, wherein said gene is introduced into $10^{10}$ to $10^{11}$ T cells.

15. The method of claim 1, wherein said introducing results in said gene being introduced into 1 to 10% of said plurality of T cells.

16. The method of claim 1, wherein steps (i), (ii), and (iii) are repeated a number of times sufficient to result in the introduction of said gene into 0.1 to 30% of said patient's T cells.

17. The method of claim 1, wherein steps (i), (ii), and (iii) are repeated a number of times sufficient to result in the introduction of such gene into 1 to 15% of said patient's T cells.

18. The method of claim 1, wherein said steps (i), (ii), and (iii) are carried out 1 to 10 times.

19. The method of claim 1, wherein said steps (i), (ii), and (iii) are carried out 2 to 5 times.

20. The method of claim 1, wherein said steps (i), (ii), and (iii) are repeated after 2 to 24 hrs.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
    ( A ) LENGTH: 5653 base pairs
    ( B ) TYPE: nucleic acid
    ( C ) STRANDEDNESS: single
    ( D ) TOPOLOGY: unknown ( i i ) MOLECULE TYPE: Other nucleic acid ( x i ) SEQUENCE DESCRIPTION: SEQ ID NO:1:

| | | | | | | |
|---|---|---|---|---|---|---|
| GACGGATCGG | GAGATCTCCC | GATCCCCTAT | GGTCGACTCT | CAGTACAATC | TGCTCTGATG | 60 |
| CCGCATAGTT | AAGCCAGTAT | CTGCTCCCTG | CTTGTGTGTT | GGAGGTCGCT | GAGTAGTGCG | 120 |
| CGAGCAAAAT | TAAGCTACA | ACAAGGCAAG | CTTGACCGA | CAATTGCATG | AAGAATCTGC | 180 |
| TTAGGGTTAG | GCGTTTTGCG | CTGCTTCGCG | ATGTACGGGC | CAGATATACG | CGTATCTGAG | 240 |
| GGGACTAGGG | TGTGTTAGG | CGAAAAGCGG | GGCTTCGGTT | GTACGCGGTT | AGGAGTCCCC | 300 |
| TCAGGATATA | GTAGTTTCGC | TTTTGCATAG | GGAGGGGAA | ATGTAGTCTT | ATGCAATACA | 360 |
| CTTGTAGTCT | TGCAACATGG | TAACGATGAG | TTAGCAACAT | GCCTTACAAG | GAGAGAAAAA | 420 |
| GCACCGTGCA | TGCCGATTGG | TGGAAGTAAG | GTGGTACGAT | CGTGCCTTAT | TAGGAAGGCA | 480 |
| ACAGACAGGT | CTGACATGGA | TTGGACGAAC | CACTGAATTC | CGCATTGCAG | AGATAATTGT | 540 |
| ATTTAAGTGC | CTAGCTCGAT | ACAATAAACG | CCATTTGACC | ATTCACCACA | TTGGTGTGCA | 600 |
| CCTCCAAGCT | CTGCTTTTTG | CCTGTACTGG | GTCTCTCTGG | TTAGACCAGA | TCTGAGCCTG | 660 |
| GGAGCTCTCT | GGCTAGCTAG | GGAACCCACT | GCTTAAGCTC | ATGGCAGGAA | GAAGCGGAGA | 720 |
| CAGCGACGAA | GACCTCCTCA | AGGCAGTCAG | ACTCATCAAG | TTTCTCTATC | AAAGCAACCC | 780 |
| ACCTCCCAAT | CCCGAGGGGA | CCCGACAGGC | CCGAAGGAAT | AGAAGAAGAA | GGTGGAGAGA | 840 |
| GAGACAGAGA | CAGATCCATT | CGATTAGTGA | ACGGATCCTT | AGCACTTATC | TGGGACGATC | 900 |
| TGCGAGCCTG | TGCCTCTTCA | GCTACCACCA | GATCTGAGAC | TTACTCTTGA | TTGTAACGAG | 960 |
| GATTGTGGAA | CTTCTGGGAC | GCAGGGGGTG | GGAAGCCCTC | AAATATTGGT | GGAATCTCCT | 1020 |
| ACAGTATTGG | AGTCAGGAAC | TAAAGAATAG | TGCTGTTAGC | TTGCTCAATG | CCACAGCTAT | 1080 |
| AGCAGTAGCT | GAGGGGACAG | ATAGGGTTAT | AGAAGTAGTA | CAAGAAGCTC | TAGAGCTCGC | 1140 |
| TGATCAGCCT | CGACTGTGCC | TTCTAGTTGC | CAGCCATCTG | TTGTTTGCCC | CTCCCCCGTG | 1200 |
| CCTTCCTTGA | CCCTGGAAGG | TGCCACTCCC | ACTGTCCTTT | CCTAATAAAA | TGAGGAAATT | 1260 |
| GCATCGCATT | GTCTGAGTAG | GTGTCATTCT | ATTCTGGGGG | GTGGGGTGGG | CAGGACAGC | 1320 |
| AAGGGGGAGG | ATTGGGAAGA | CAATAGCAGG | CATGCTGGGG | ATGCGGTGGG | CTCTATGGCT | 1380 |
| TCTGAGGCGG | AAAGAACCAG | CTGGGGCTCG | AGGGGGGATC | CCCACGCGCC | CTGTAGCGGC | 1440 |
| GCATTAAGCG | CGGCGGGTGT | GGTGGTTACG | CGCAGCGTGA | CCGCTACACT | TGCCAGCGCC | 1500 |
| CTAGCGCCCG | CTCCTTTCGC | TTTCTTCCCT | TCCTTTCTCG | CCACGTTCGC | CGGCTTTCCC | 1560 |
| CGTCAAGCTC | TAAATCGGGG | CATCCCTTTA | GGGTTCCGAT | TTAGTGCTTT | ACGGCACCTC | 1620 |
| GACCCCAAAA | AACTTGATTA | GGGTGATGGT | TCACGTAGTG | GGCCATCGCC | CTGATAGACG | 1680 |
| GTTTTTCGCC | CTTTGACGTT | GGAGTCCACG | TTCTTTAATA | GTGGACTCTT | GTTCCAAACT | 1740 |
| GGAACAACAC | TCAACCCTAT | CTCGGTCTAT | TCTTTTGATT | TATAAGGGAT | TTTGGGGATT | 1800 |

| | | | | | |
|---|---|---|---|---|---|
| TCGGCCTATT | GGTTAAAAAA | TGAGCTGATT | TAACAAAAAT | TTAACGCGAA | TTTTAACAAA | 1860
| ATATTAACGT | TTACAATTTA | AATATTTGCT | TATACAATCT | TCCTGTTTTT | GGGGCTTTTC | 1920
| TGATTATCAA | CCGGGGTGGG | TACCGAGCTC | GAATTCTGTG | GAATGTGTGT | CAGTTAGGGT | 1980
| GTGGAAAGTC | CCCAGGCTCC | CCAGGCAGGC | AGAAGTATGC | AAAGCATGCA | TCTCAATTAG | 2040
| TCAGCAACCA | GGTGTGGAAA | GTCCCCAGGC | TCCCCAGCAG | CAGAAGTAT | GCAAAGCATG | 2100
| CATCTCAATT | AGTCAGCAAC | CATAGTCCCG | CCCCTAACTC | CGCCCATCCC | GCCCCTAACT | 2160
| CCGCCCAGTT | CCGCCCATTC | TCCGCCCCAT | GGCTGACTAA | TTTTTTTTAT | TTATGCAGAG | 2220
| GCCGAGGCCG | CCTCGGCCTC | TGAGCTATTC | CAGAAGTAGT | GAGGAGGCTT | TTTTGGAGGC | 2280
| CTAGGCTTTT | GCAAAAAGCT | CCCGGGAGCT | TGGATATCCA | TTTTCGGATC | TGATCAAGAG | 2340
| ACAGGATGAG | GATCGTTTCG | CATGATTGAA | CAAGATGGAT | TGCACGCAGG | TTCTCCGGCC | 2400
| GCTTGGGTGG | AGAGGCTATT | CGGCTATGAC | TGGGCACAAC | AGACAATCGG | CTGCTCTGAT | 2460
| GCCGCCGTGT | TCCGGCTGTC | AGCGCAGGGG | CGCCCGGTTC | TTTTTGTCAA | GACCGACCTG | 2520
| TCCGGTGCCC | TGAATGAACT | GCAGGACGAG | GCAGCGCGGC | TATCGTGGCT | GGCCACGACG | 2580
| GGCGTTCCTT | GCGCAGCTGT | GCTCGACGTT | GTCACTGAAG | CGGGAAGGGA | CTGGCTGCTA | 2640
| TTGGGCGAAG | TGCCGGGGCA | GGATCTCCTG | TCATCTCACC | TTGCTCCTGC | CGAGAAAGTA | 2700
| TCCATCATGG | CTGATGCAAT | GCGGCGGCTG | CATACGCTTG | ATCCGGCTAC | CTGCCCATTC | 2760
| GACCACCAAG | CGAAACATCG | CATCGAGCGA | GCACGTACTC | GGATGGAAGC | CGGTCTTGTC | 2820
| GATCAGGATG | ATCTGGACGA | AGAGCATCAG | GGGCTCGCGC | CAGCCGAACT | GTTCGCCAGG | 2880
| CTCAAGGCGC | GCATGCCCGA | CGGCGAGGAT | CTCGTCGTGA | CCCATGGCGA | TGCCTGCTTG | 2940
| CCGAATATCA | TGGTGGAAAA | TGGCCGCTTT | TCTGGATTCA | TCGACTGTGG | CCGGCTGGGT | 3000
| GTGGCGGACC | GCTATCAGGA | CATAGCGTTG | GCTACCCGTG | ATATTGCTGA | AGAGCTTGGC | 3060
| GGCGAATGGG | CTGACCGCTT | CCTCGTGCTT | TACGGTATCG | CCGCTCCCGA | TTCGCAGCGC | 3120
| ATCGCCTTCT | ATCGCCTTCT | TGACGAGTTC | TTCTGAGCGG | GACTCTGGGG | TTCGAAATGA | 3180
| CCGACCAAGC | GACGCCCAAC | CTGCCATCAC | GAGATTTCGA | TTCCACCGCC | GCCTTCTATG | 3240
| AAAGGTTGGG | CTTCGGAATC | GTTTTCCGGG | ACGCCGGCTG | GATGATCCTC | CAGCGCGGGG | 3300
| ATCTCATGCT | GGAGTTCTTC | GCCCACCCCA | ACTTGTTTAT | TGCAGCTTAT | AATGGTTACA | 3360
| AATAAAGCAA | TAGCATCACA | AATTTCACAA | ATAAAGCATT | TTTTCACTG | CATTCTAGTT | 3420
| GTGGTTTGTC | CAAACTCATC | AATGTATCTT | ATCATGTCTG | GATCCCGTCG | ACCTCGAGAG | 3480
| CTTGGCGTAA | TCATGGTCAT | AGCTGTTTCC | TGTGTGAAAT | TGTTATCCGC | TCACAATTCC | 3540
| ACACAACATA | CGAGCCGGAA | GCATAAAGTG | TAAAGCCTGG | GGTGCCTAAT | GAGTGAGCTA | 3600
| ACTCACATTA | ATTGCGTTGC | GCTCACTGCC | CGCTTTCCAG | TCGGGAAACC | TGTCGTGCCA | 3660
| GCTGCATTAA | TGAATCGGCC | AACGCGCGGG | GAGAGGCGGT | TTGCGTATTG | GGCGCTCTTC | 3720
| CGCTTCCTCG | CTCACTGACT | CGCTGCGCTC | GGTCGTTCGG | CTGCGGCGAG | CGGTATCAGC | 3780
| TCACTCAAAG | GCGGTAATAC | GGTTATCCAC | AGAATCAGGG | GATAACGCAG | GAAAGAACAT | 3840
| GTGAGCAAAA | GGCCAGCAAA | AGGCCAGGAA | CCGTAAAAAG | GCCGCGTTGC | TGGCGTTTTT | 3900
| CCATAGGCTC | CGCCCCCCTG | ACGAGCATCA | CAAAAATCGA | CGCTCAAGTC | AGAGGTGGCG | 3960
| AAACCCGACA | GGACTATAAA | GATACCAGGC | GTTTCCCCCT | GGAAGCTCCC | TCGTGCGCTC | 4020
| TCCTGTTCCG | ACCCTGCCGC | TTACCGGATA | CCTGTCCGCC | TTTCTCCCTT | CGGGAAGCGT | 4080
| GGCGCTTTCT | CAATGCTCAC | GCTGTAGGTA | TCTCAGTTCG | GTGTAGGTCG | TTCGCTCCAA | 4140
| GCTGGGCTGT | GTGCACGAAC | CCCCCGTTCA | GCCCGACCGC | TGCGCCTTAT | CCGGTAACTA | 4200

-continued

| | | | | | |
|---|---|---|---|---|---|
| TCGTCTTGAG | TCCAACCCGG | TAAGACACGA | CTTATCGCCA | CTGGCAGCAG | CCACTGGTAA | 4260
| CAGGATTAGC | AGAGCGAGGT | ATGTAGGCGG | TGCTACAGAG | TTCTTGAAGT | GGTGGCCTAA | 4320
| CTACGGCTAC | ACTAGAAGGA | CAGTATTTGG | TATCTGCGCT | CTGCTGAAGC | CAGTTACCTT | 4380
| CGGAAAAAGA | GTTGGTAGCT | CTTGATCCGG | CAAACAAACC | ACCGCTGGTA | GCGGTGGTTT | 4440
| TTTTGTTTGC | AAGCAGCAGA | TTACGCGCAG | AAAAAAAGGA | TCTCAAGAAG | ATCCTTTGAT | 4500
| CTTTTCTACG | GGGTCTGACG | CTCAGTGGAA | CGAAAACTCA | CGTTAAGGGA | TTTTGGTCAT | 4560
| GAGATTATCA | AAAAGGATCT | TCACCTAGAT | CCTTTTAAAT | TAAAAATGAA | GTTTTAAATC | 4620
| AATCTAAAGT | ATATATGAGT | AAACTTGGTC | TGACAGTTAC | CAATGCTTAA | TCAGTGAGGC | 4680
| ACCTATCTCA | GCGATCTGTC | TATTTCGTTC | ATCCATAGTT | GCCTGACTCC | CCGTCGTGTA | 4740
| GATAACTACG | ATACGGGAGG | GCTTACCATC | TGGCCCCAGT | GCTGCAATGA | TACCGCGAGA | 4800
| CCCACGCTCA | CCGGCTCCAG | ATTTATCAGC | AATAAACCAG | CCAGCCGGAA | GGGCCGAGCG | 4860
| CAGAAGTGGT | CCTGCAACTT | TATCCGCCTC | CATCCAGTCT | ATTAATTGTT | GCCGGGAAGC | 4920
| TAGAGTAAGT | AGTTCGCCAG | TTAATAGTTT | GCGCAACGTT | GTTGCCATTG | CTACAGGCAT | 4980
| CGTGGTGTCA | CGCTCGTCGT | TTGGTATGGC | TTCATTCAGC | TCCGGTTCCC | AACGATCAAG | 5040
| GCGAGTTACA | TGATCCCCCA | TGTTGTGCAA | AAAAGCGGTT | AGCTCCTTCG | GTCCTCCGAT | 5100
| CGTTGTCAGA | AGTAAGTTGG | CCGCAGTGTT | ATCACTCATG | GTTATGGCAG | CACTGCATAA | 5160
| TTCTCTTACT | GTCATGCCAT | CCGTAAGATG | CTTTTCTGTG | ACTGGTGAGT | ACTCAACCAA | 5220
| GTCATTCTGA | GAATAGTGTA | TGCGGCGACC | GAGTTGCTCT | TGCCCGGCGT | CAATACGGGA | 5280
| TAATACCGCG | CCACATAGCA | GAACTTTAAA | AGTGCTCATC | ATTGGAAAAC | GTTCTTCGGG | 5340
| GCGAAAACTC | TCAAGGATCT | TACCGCTGTT | GAGATCCAGT | TCGATGTAAC | CCACTCGTGC | 5400
| ACCCAACTGA | TCTTCAGCAT | CTTTTACTTT | CACCAGCGTT | TCTGGGTGAG | CAAAAACAGG | 5460
| AAGGCAAAAT | GCCGCAAAAA | AGGGAATAAG | GGCGACACGG | AAATGTTGAA | TACTCATACT | 5520
| CTTCCTTTTT | CAATATTATT | GAAGCATTTA | TCAGGGTTAT | TGTCTCATGA | GCGGATACAT | 5580
| ATTTGAATGT | ATTTAGAAAA | ATAAACAAAT | AGGGGTTCCG | CGCACATTTC | CCCGAAAAGT | 5640
| GCCACCTGAC | GTC | | | | | 5653